(12) United States Patent
Colasanti et al.

(10) Patent No.: US 6,813,615 B1
(45) Date of Patent: Nov. 2, 2004

(54) METHOD AND SYSTEM FOR INTERPRETING AND VALIDATING EXPERIMENTAL DATA WITH AUTOMATED REASONING

(75) Inventors: Ricardo L. Colasanti, South Glamorgan (GB); Mark A. D. Collins, Sully Vale of Glamorgan (GB); John R. Shaw, Romsey (GB)

(73) Assignee: Cellomics, Inc., Pittsburgh, PA (US)

( * ) Notice: Subject to any disclaimer, the term of this patent is extended or adjusted under 35 U.S.C. 154(b) by 236 days.

(21) Appl. No.: 09/656,372

(22) Filed: Sep. 6, 2000

(51) Int. Cl.[7] .............................. G06F 17/00; G06N 5/00
(52) U.S. Cl. .............................. 706/46; 706/45; 706/47
(58) Field of Search ............................. 706/45, 46, 47; 704/9

(56) References Cited

U.S. PATENT DOCUMENTS

| | | | |
|---|---|---|---|
| 4,942,526 A | 7/1990 | Okajima et al. | |
| 5,181,163 A | 1/1993 | Nakajima et al. | |
| 5,235,522 A | 8/1993 | Bacus | |
| 5,263,126 A | 11/1993 | Chang | |
| 5,276,860 A | 1/1994 | Fortier et al. | |

(List continued on next page.)

FOREIGN PATENT DOCUMENTS

| | | |
|---|---|---|
| EP | 0 367 544 A2 | 5/1990 |
| WO | WO 91/06050 A1 | 5/1991 |
| WO | WO 96/22575 A1 | 7/1996 |
| WO | WO98/15825 | 4/1998 |
| WO | WO 98/38490 A1 | 9/1998 |
| WO | WO99/05323 | 2/1999 |
| WO | WO 00/15847 | 3/2000 |

OTHER PUBLICATIONS

W. Salmonsen, K.Y.C. Mok, P. Kolatkar, S. Subbiah, "Bio-JAKE: A Tool for the Creation, Visualization and Manipulation of Metabolic Pathways," Bioinformatics Centre, Jan. 1999, pp. 392–400.

W. Fujibuchi, K. Sato, H. Ogata, S. Goto, M. Kanehisa, "KEGG and DBGET/LinkDB: Integration of Biological Relationships in Divergent Molecular Biology Data," Institute for Chemical Research, Kyoto University, 1998, pp. 35–40.

(List continued on next page.)

Primary Examiner—Wilbert L. Starks, Jr.
Assistant Examiner—Joseph P. Hirl
(74) Attorney, Agent, or Firm—McDonnell Boehnen Hulbert & Berghoff LLP

(57) ABSTRACT

A method and system for interpreting experimental data with automated reasoning. Domain specific knowledge is acquired from one or more pharmaceutical information sources. A semantic representation of the domain specific knowledge is created meeting a desired set of criteria. Pharmaceutical data from a knowledge database is classified with the semantic representation, allowing construction of a set of reasons for any classified pharmaceutical data. The set of reasons may help interpret the classified pharmaceutical data to remove errors, such as "physical errors" and "biological errors". Removing such errors helps improve fusion of knowledge from multiple data, information and knowledge sources which incorporates activity and selectivity against a target, desired pharmacokinetic and toxicity properties enabling selection of potential pharmaceutical compounds. The method and system may improve identification, selection, validation and screening of new real or virtual pharmaceutical compounds or may be used to provide bioinformatic techniques for storing and manipulating pharmaceutical knowledge.

20 Claims, 15 Drawing Sheets

U.S. PATENT DOCUMENTS

| | | | |
|---|---|---|---|
| 5,276,867 A | 1/1994 | Kenley et al. | |
| 5,287,497 A | 2/1994 | Behera | |
| 5,307,287 A | 4/1994 | Cramer, III et al. | |
| 5,355,445 A | 10/1994 | Shibao et al. | |
| 5,379,366 A | 1/1995 | Noyes | |
| 5,418,943 A | 5/1995 | Borgida et al. | |
| 5,418,944 A | 5/1995 | DiPace et al. | |
| 5,511,186 A | 4/1996 | Carhart et al. | |
| 5,554,505 A | 9/1996 | Hajek et al. | |
| 5,615,112 A | 3/1997 | Liu Sheng et al. | |
| 5,657,255 A | 8/1997 | Fink et al. | |
| 5,675,819 A | 10/1997 | Schuetze | |
| 5,742,811 A | 4/1998 | Agrawal et al. | |
| 5,751,605 A | 5/1998 | Hurst et al. | |
| 5,806,060 A | 9/1998 | Borgida et al. | |
| 5,808,918 A | 9/1998 | Fink et al. | |
| 5,809,499 A | 9/1998 | Wong et al. | |
| 5,819,266 A | 10/1998 | Agrawal et al. | |
| 5,857,185 A | 1/1999 | Yamaura | |
| 5,862,514 A | 1/1999 | Huse et al. | |
| 5,873,080 A | 2/1999 | Coden et al. | |
| 5,873,083 A | 2/1999 | Jones et al. | |
| 5,892,838 A | 4/1999 | Brady | |
| 5,901,069 A | 5/1999 | Agrafiotis et al. | |
| 5,914,891 A | 6/1999 | McAdams et al. | |
| 5,930,154 A | 7/1999 | Thalhammer-Reyero | |
| 5,940,817 A | 8/1999 | Kishi et al. | |
| 5,950,192 A | 9/1999 | Moore et al. | |
| 5,965,352 A | 10/1999 | Stoughton et al. | |
| 5,966,712 A | 10/1999 | Sabatini et al. | |
| 5,970,482 A | 10/1999 | Pham et al. | |
| 5,970,500 A | 10/1999 | Sabatini et al. | |
| 5,978,804 A | 11/1999 | Dietzman | |
| 5,980,096 A | 11/1999 | Thalhammer-Reyero | |
| 6,023,659 A | 2/2000 | Seilhamer et al. | |
| 6,073,138 A | 6/2000 | de l'Etraz et al. | |
| 6,081,620 A | 6/2000 | Anderholm | |
| 6,094,652 A | 7/2000 | Faisal | |
| 6,103,479 A | 8/2000 | Taylor | |
| 6,199,034 B1 * | 3/2001 | Wical | 704/9 |

OTHER PUBLICATIONS

P.D. Karp, "Database Links are a Foundation for Interoperability," Aug. 1996, pp. 273–279, TibTech, (vol. 14).

Paley, P.D. Karp, "Adapting EcoCyc for Use on the World Wide Web," Gene 172 (1996) GC43–GC50, Mar. 28, 1996, pp. 43–50.

P.D. Karp, "Computer Corner–Metabolic Databases," Mar. 23, 1998, pp. 114–116, TIBS.

C. Allee, "Data Management for Automated Drug Discovery Laboratories," XP–002134398, Aug. 21, 1996, pp. 307–310.

A.R. Kerlavage, W. FitzHugh, A. Glodek, J. Kelley, J. Scott, R. Shirley, G. Sutton, Man Wai–Chiu, O. White, M.D. Adams, "Data Management and Analysis for High–Throughput DNA Sequencing Projects," IEEE Engineering in Medicine and Biology, Nov./Dec. 1995, pp. 710–717.

K.A. Giuliano, D. Lansing Taylor, "Flourescent–Protein Biosensors: New Tools for Drug Discovery," Mar. 1998, pp. 135–140, TibTech (vol. 16).

Cellomics Vital Knowledge, Smarter Screening and Lead Optimization with Cellomics™ High content Screening Systems and Informatics Tools In An Integrated Drug Discovery Solution. 1999.

K.A. Giuliano, R.L. DeBiasio, R. T.Dunlay, A. Gough, J.M. Volosky, J. Zock, G.N. Pavlakis, D. Lansing Taylor, "High–Content Screening: A New Approach to Easing Key Bottlenecks in the Drug Discovery Process," Journal of Biomolecular Screening, 1997, pp. 249–259, (vol. 2, No. 4) Winter.

B.R. Conway, L.K. Minor, J.Z. Xu, J.W. Gunnet, R. DeBiasio, M.R. D'Andrea, R. Rubin, R. DeBiasio, K. Giuliano, L. Zhou, K.T. Demarest, "Quantification of G–aprotein Couples Receptor Internalization Using G–Protein Coupled Receptor–Green Flourescent Protein Conjugates with the ArrayScan™ High–Content Screening System," Journal of Biomolecular Screening, 1999, pp. 75–86, (vol. , No. 2), Apr.

Ethan B. Arutunian, Deirdre R. Meldrum, Neal A. Friedman and Stephen E. Moody, "Flexible Software Architecture for User–Interface and Machine Control in Laboratory Automation," BioTechniques 25:698–705 (Oct. 1998).

Blaschke et al., "Automatic Extraction Of Biological Information From Scientific Text: Protein–Protein Interactions", ISMB'99, pp. 60–67.

Chen et al., "Automatic Construction Of Networks Of Concepts Characterizing Document Databases", IEEE Transactions On Systems, Man, And Cybernetics, vol. 22, No. 5, Sep./Oct. 1992, pp. 885–902.

Chen et al., "An Algorithmic Approach To Concept Exploration In A Large Knowledge Network (Automatic Thesaurus Consultation): Symbolic Branch–And–Bound Search vs. Connectionist Hopfield Net Activation", Journal Of The American Society For Information Science, 3615), 1995, pp. 348–369.

Craven et al., "Constructing Biological Knowledge Bases By Extracting Information From Text Sources", ISMB'99, pp. 77–86.

Gordon et al., "Toward Discovery Support Systems: A Replication, Re–Examination, And Extension Of Swanson's Work On Literature–Based Discovery Of A Connection Between Raynaud's And Fish Oil", Journal Of The American Society For Information Science, 47(2), 1996, pp. 116–128.

Swanson et al., "An Interactive System For Finding Complementary Literatures: A Stimulus To Scientrlic Discovery", Artifical Intelligence 91 (1997), pp. 183–203.

Overbeek et al., "Representation of Function: The Next Step", Pub. On–line Jan. 31, 1997, www.mcs.anl.gov/compbio/publications/function_pap.html, pp. 1–13.

* cited by examiner

FIG. 15
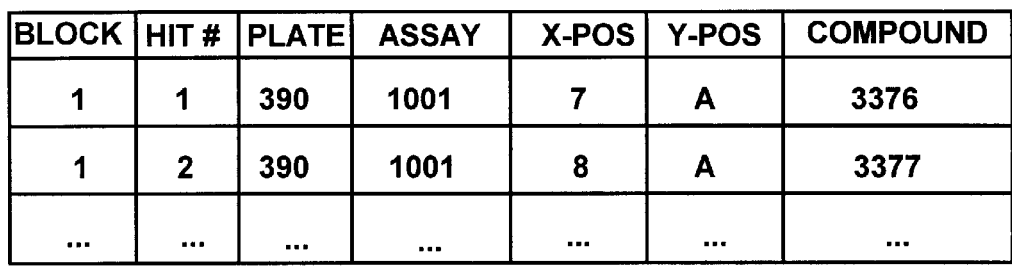
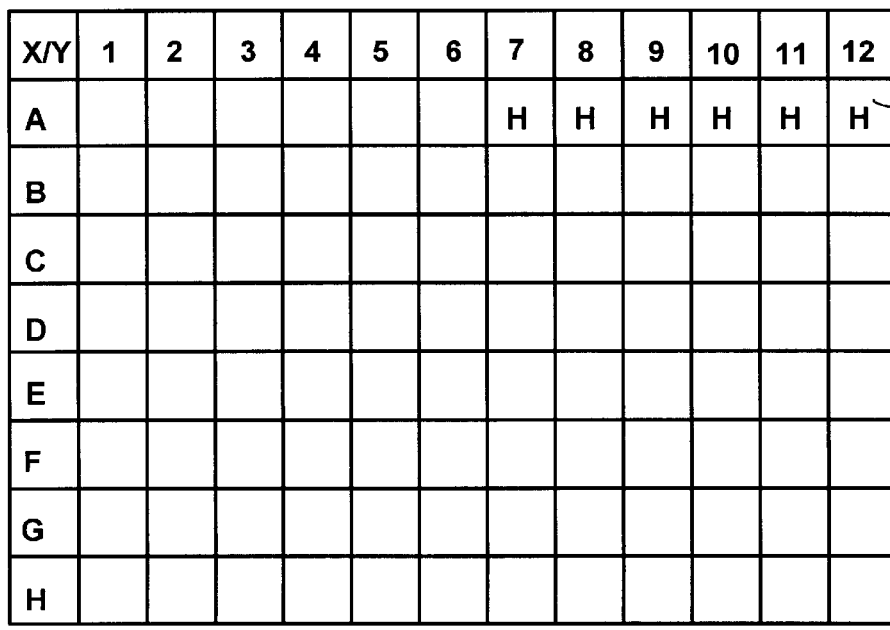
REPORT:
A SUSPECT ERROR DATA BLOCK OF SIX HITS IN ASSAY 1001 IN PLATE 390 HAS BEEN DETECTED. THIS POSSIBLY A CLOGGED PIPETTE ERROR.

METHOD AND SYSTEM FOR INTERPRETING AND VALIDATING EXPERIMENTAL DATA WITH AUTOMATED REASONING

FIELD OF THE INVENTION

This invention relates to analyzing experimental data. More specifically, it relates to methods and system for identifying potential pharmaceutical drug candidates by interpreting and validating errors in experimental data with automated reasoning.

BACKGROUND OF THE INVENTION

Historically, the discovery and development of new drugs has been an expensive, time consuming and inefficient process, With estimated costs of bringing a single drug to market requiring an investment of approximately 8 to 12 years and approximately $350 to $610 million, the pharmaceutical industry is in need of new technologies that can streamline the drug discovery process. Companies in the pharmaceutical industry are under fierce pressure to shorten research and development cycles for developing new drugs, while at the same time, novel drug discovery screening instrumentation technologies are being deployed, producing a huge amount of experimental data (e.g., gigabytes per day).

To fully exploit the potential of experimental data from high-volume data generating screening instrumentation, there is a need for new informatic and bioinformatic tools. As is known in the art, "bioinformatic" techniques are used to address problems related to the collection, processing, storage, retrieval and analysis of biological information including cellular information. Bioinformatics is defined as the systematic development and application of information technologies and data processing techniques for collecting, analyzing and displaying data obtained by experiments, modeling, database searching, and instrumentation to make observations about biological processes. Bioinformatic tools are being used to process experimental data to create and manipulate knowledge stores.

As is known in the art, "knowledge" includes a body of truth, information, expertise or principals obtained through the application of reasoning to facts or data. Knowledge is used for some task, e.g., to modify behavior based upon information and experience. A common view of knowledge is that it includes more value than mere data and information. At one level it is accepted that knowledge is something that mainly resides in the "heads of individuals" i.e., experience that divides an expert from a non-expert in a particular domain. Terms such as "Use of Knowledge" or "Knowledge Management,""Knowledge Capital", "Knowledge Assets," "Business Intelligence" and "Knowledge Culture" are becoming common in the pharmaceutical industry and industry in general.

One problem is that at best, knowledge in corporate databases can only be considered as declarative knowledge (i.e., information in computer readable form) or method and process knowledge (i.e., basic mathematical relationships). Another problem is that knowledge is viewed at some gross level as "just information" and thus the key to knowledge management is to improve information systems in some way.

Another problem is that there are many diverse approaches to knowledge storage and management. These knowledge storage and management approaches include, for example, basic repository; experience repository; corporate personal expertise base; knowledge transfer; knowledge culture; enhanced repository knowledge server; corporate rule based; data mining and data visualization; and data warehouse, datamart, Online Analytical Processing (OLAP) coupled to Executive (EIS)-or Management (MIS) Information System.

The basic repository includes knowledge extracted from human experts by some means and stored in a system for later access. The knowledge is mostly structured and primarily in the form of documents. The experience repository includes knowledge that is much less structured and in the form of insights and observations of experts, usually in the form of documents or threaded discussion databases. The corporate personal expertise base does not include knowledge as such but typically provides pointers to those individuals who do have knowledge. Knowledge transfer includes some means of transferring knowledge from individuals to other individuals. Knowledge culture includes knowledge promoted from a human resource perspective appreciation, value of knowledge and a culture of knowledge sharing.

Enhanced repository knowledge servers include an automated indexing, cross-referencing, annotation and presentation of information, with the expectation that this will lead to knowledge in some way. Corporate rule based includes knowledge from a true knowledge base using expert system technology to extract and codify knowledge into business rules that can be applied to information and data.

Data mining includes knowledge obtained from patterns in multidimensional data and then annotating those patterns to give them value. Data visualization includes transforming knowledge obtained from three-dimensional graphs to visual pattern representations. Data warehouse, data-mart, online analytical processing coupled to executive information systems or management information systems include knowledge obtained from business rules to summarize data and information into a second database where it is more readily accessible. Tools then present the enhanced information in various views, with drill down etc., so that an individual will be able to create the knowledge. These knowledge management and storage approaches differ widely, both in their manner and the technology used.

Another problem is that none of these approaches address managing knowledge in all of its forms throughout a business or multiple businesses and then using that knowledge as a fundamental driver of business. Another problem is that the whole drive towards knowledge management is in itself fundamentally flawed since it is the ability to use knowledge to change corporate behavior that is the real problem; the power to act on knowledge being one of most important factors of knowledge use.

The pharmaceutical, telecommunications, banking, aeronautical engineering, retail supermarkets, insurance companies and others are some of the commercial sectors that are applying knowledge based approaches at varying levels to successfully drive their business with knowledge. These industries are receiving very high returns in some cases (e.g., British-Telecom (UK) estimates implementing a knowledge based strategy for network maintenance scheduling will provide cost savings of 1 billion pounds per year).

Some of the companies that have implemented knowledge strategies to drive their businesses indicate that one or more of the following knowledge criteria need to be satisfied: (1) knowledge is extracted from a particular domain/discipline or business process (from experts, databases etc), in the form of rules or models of reality; (2) knowledge is encapsulated (usually into some form of software); (3) knowledge is delivered and used, either via, or within a conventional information infrastructure; (4) knowledge is used, together with data and information to change business behavior; and (5) knowledge management is combined with organizational re-structuring in order to best use knowledge; ideally the restructuring itself is driven by knowledge, and new knowledge and refinement of old knowledge can be accommodated. Note that in many cases all these criteria were not present in the approaches used by such companies and the points above represent an idealized case.

However, few companies that have applied such knowledge management strategies have applied it to their entire business, or structured a business or business division completely around knowledge management. Knowledge management is thus seen as an add-on rather than the foundation of a business. Thus, it is important that knowledge management in drug discovery should be a business foundation rather than an add-on.

Another problem is that as drug discovery becomes more and more complex, knowledge storage and management become more and more specialized and compartmentalized. The pharmaceutical industry typically has as many as 7,000 compounds in active development at any one time. It is already questionable whether the pharmaceutical industry can support this numerical level of drug development, especially when at the end of the process the number of new drugs entering the market has not shown any increase.

One optimistic viewpoint is that it is perhaps too early for drug candidates derived from the new discovery technologies such as high throughput screening to have progressed to late development and market. Alternatively, there is, and will continue to be, an increasing "attrition rate" of new compounds that start active development but never reach market. This high attrition rate has cost implications, as successful drugs must support the increasing number of drug candidate failures.

New technologies (e.g., high throughput screening) may therefore simply increase the number of compounds available for active development, a number perhaps in excess of one million at any one time and further aggravate the discovery problem. Since there is already a huge shortfall of compounds completing development (e.g., a 1 in 10 success rate), use of knowledge storage and management techniques known in the art are not improving the attrition rate for pharmaceutical compounds.

One of the key goals of the pharmaceutical industry is to reduce the attrition rate among new drug candidates accepted for development using knowledge. Thus, the need for decision making/support systems based on knowledge has been identified as "critical" to address the attrition rate for new drug candidates.

One problem associated with reducing the attrition rate is that it is difficult to determine errors in pharmaceutical data collected from automated screening systems. When automated screening systems are used there are almost always common "physical screening problems" related to instrument and/or equipment errors (e.g., a clogged or partially clogged pipette head), common microplate preparation errors, microplate variances within runs, bio-chip problems, gel-electrophoresis problems, etc. It is desirable to remove such-physical errors and others to improve interpretation and validation of any knowledge that is created.

Another problem is that "biological specific errors" such as errors in assays can also occur during automated screening. It is also desirable to remove biological errors when possible to improve any new knowledge generated from such pharmaceutical data. Therefore, it is desirable to provide an improved method and system to detect data collected for the pharmaceutical and other industries. The method and system should include the ability to identify and manipulate error data associated with physical as well as biological errors.

SUMMARY OF THE INVENTION

In accordance with preferred embodiments of the present invention, some of the problems associated with removing errors from experimental data from automated screening systems are overcome. A method and system for interpreting and validating experimental data are presented.

Pharmaceutical data from a knowledge database is classified with a semantic representation. A set of reasons for any classified pharmaceutical data is provided. The set of reasons are used to help interpret the classified pharmaceutical data to remove errors such as "physical errors" (e.g., pipetter errors, common microplate preparation errors, microplate variances within runs, bio-chip errors, gel-electrophoresis errors, etc.) and "biological specific errors" such as errors in assays.

The method and system may be used to improve the identification, selection, validation and screening of new real or virtual pharmaceutical compounds by removing physical and/or biological specific errors in pharmaceutical data. The method and system may also be used to provide new bioinformatic techniques for storing and manipulating pharmaceutical knowledge.

The foregoing and other features and advantages of preferred embodiments of the present invention will be more readily apparent from the following detailed description. The detailed description proceeds with references to the accompanying drawings.

BRIEF DESCRIPTION OF THE DRAWINGS

Preferred embodiments of the present invention are described with reference to the following drawings, wherein:

FIG. 15 is a block diagram visually illustrating exemplary output from the method of FIG. 14.

DETAILED DESCRIPTION OF PREFERRED EMBODIMENTS

EXEMPLARY KNOWLEDGE SYSTEM

Figure 1:
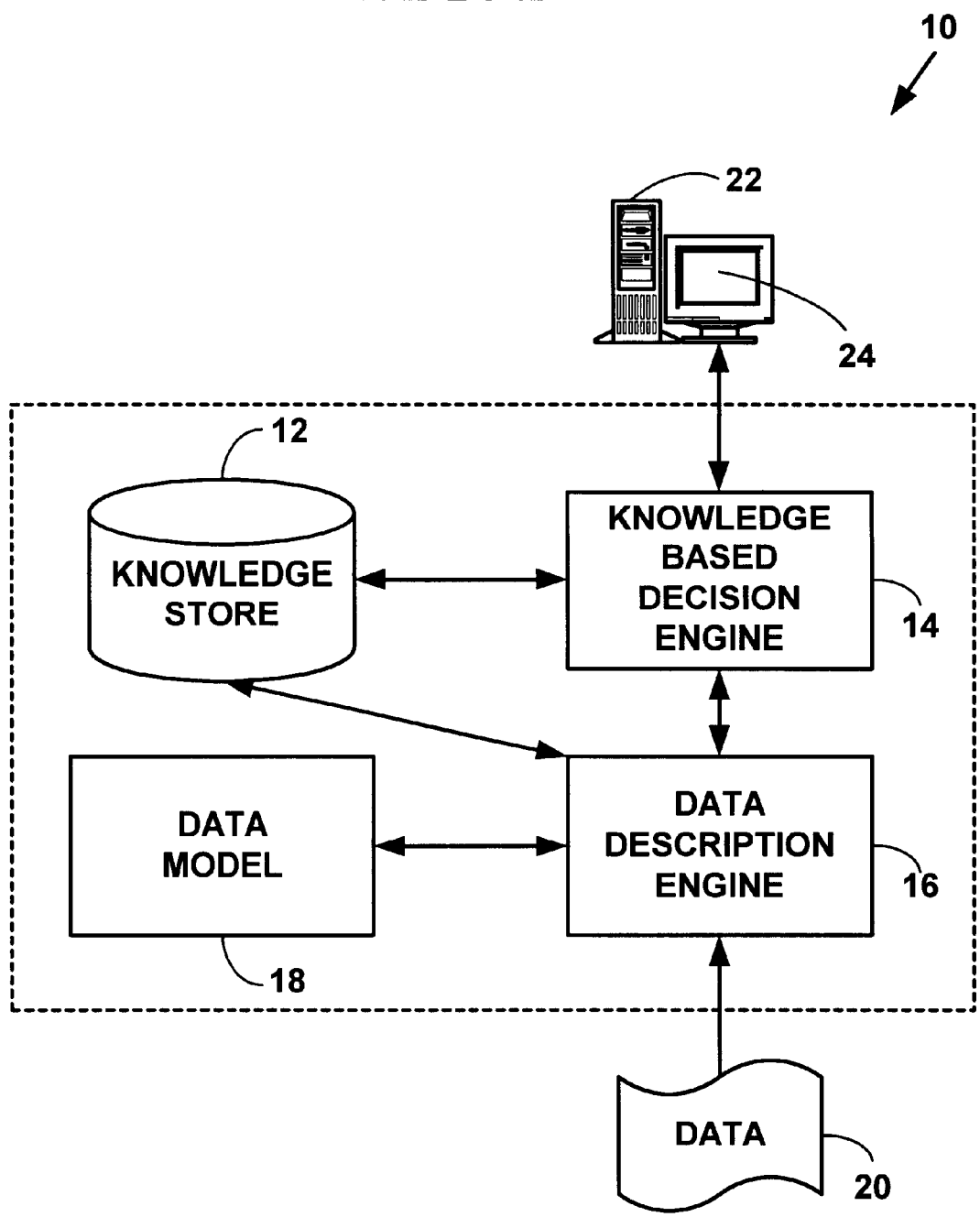
FIG. 1 illustrates an exemplary knowledge system.

FIG. 1 illustrates an exemplary knowledge system 10 for one embodiment of the present invention. The knowledge system 10 includes a knowledge database or store 12, a knowledge based decision engine 14, a data description engine 16, a data description model 18, and knowledge data 20. The knowledge system 10 also includes a user computer 22 with an optional graphical user interface 24. However, the present invention is not limited to such an embodiment and more, fewer or equivalent components can also be used.

In such an embodiment, the knowledge store 12 includes raw experimental data and knowledge derived from the raw experimental data. The knowledge store comprises one or more multi-user, multi-view databases that store experimental data and derived knowledge. The knowledge store 12 uses relational database tools and structures. The knowledge store 12 is accessible using selected security features (e.g., login, password, firewall, etc.).

The knowledge based decision engine 14 provides functionality to extract raw data and derived knowledge from the knowledge store 12, and encapsulate it into knowledge objects.

In-preferred embodiments of the present invention, experimental data includes any result returned from one or more operations carried out under controlled conditions to discover an unknown or prove a hypothesis. Experimental data includes data obtained from high throughput screen systems, data obtained from database queries, spread sheet analysis, document analysis, visual interpretation of data and from other sources. The Experimental data is not limited to data obtained from laboratory experiments but also includes socio-economic and other types of data. However, the present invention is not limited to experimental data with these characteristics, and more fewer or equivalent characteristics can also be used to define experimental data.

In preferred embodiments of the present invention, knowledge includes: (1) a knowing or familiarity of a domain gained by experiencing that domain by some means; (2) a theoretical or practical understanding of a domain, where the understanding exists as a theory or opinion that has been empirically or experimentally verified by a community; and (3) a basis of intelligence and provides the ability to turn raw data and information into a form to support real world decisions. However, the present invention is not limited to experimental data with these characteristics, and more fewer or equivalent characteristics can also be used to define experimental data.

The raw experimental data and derived knowledge is fused with other knowledge to create "fused knowledge." Knowledge fusion is not a sequential process where one knowledge component is delivered followed by another, but rather a summary of knowledge that is processed in parallel. Knowledge fusion modifies the contribution of available knowledge components in order to deliver the knowledge to best solve a desired problem. Knowledge fusion includes evolutionary and adaptive features to dynamically manage knowledge.

The data description engine 16 provides dynamic object-based wrapping of knowledge data 20 from virtually any data source. The data description engine 16 is an interface to the knowledge data 20 and applies the data model 18 to the knowledge data 20 that is used by the knowledge based decision engine 14. In one embodiment of the present invention, the data description engine 16 uses a "semantic approach" to process knowledge data 20 with the data model 18 based on drug discovery terminology and relationships to create derived knowledge. As is known in the art, a "semantic approach" includes applying relationship between words or symbols and their intended meanings and to represent relationships among objects, ideas, or situations with a set of rules. However, the present invention is not limited to such an embodiment, and the data description engine 16 can be used provide dynamic object-based wrapping of virtually any type of data for virtually any domain.

The description data model 18 is a universal data model and framework that allows raw experimental data and derived knowledge to be stored regardless of virtually any initial format. The descriptive data model 18 allows data to be processed in a manner relevant to a predetermined process (e.g., a business process). In one embodiment of the present invention, the data model 18 permits processing and storage of parallel, virtual parallel, multi-parameter and virtual multi-parameter drug discovery screening data to be managed and processed. "Virtual parallel" relates to the creation of new computer generated data entities derived from real or computer generated data, "virtual multi-parameter" relates to the creation of new computer generated data entities derived from real or computer generated data originating from instrumentation capable of reading more than one parameter. The data model 18 includes real as well as virtual data components.

In one embodiment of the present invention, the data model 18 includes optimized data components for storing drug discovery information. These optimized data components are derived from an object level, semantically grounded analysis of the entire drug discovery business process. However, the present invention is not limited to such an embodiment and virtually any type of experimental and or analytical data can be stored with the data model 18.

The knowledge data 20 includes raw experimental data from experiments and derived knowledge. The derived knowledge includes knowledge derived from raw experimental data using one or more iterative knowledge creation techniques. In one embodiment of the present invention, the experimental data 20 includes raw experimental data and derived knowledge from drug discovery experiments. However, the present invention is not limited to such an embodiment and virtually any type of experimental data and derived knowledge can also be used.

The user computer 22 is a conventional personal computer that includes a display application that provides a Graphical User Interface ("GUI") 24. The GUI 24 or a non-graphical command line interface is used to lead a manager, scientist or lab technician through input, retrieval and analysis of knowledge and supports custom viewing capabilities. The GUI 24 also supports data exported into standard desktop tools such as spreadsheets, graphics packages, and word processors.

In one specific embodiment of the present invention, one or more protocols from the Internet Suite of protocols are used with knowledge system 10. As is known in the art, the Internet Suite of protocols includes such protocols as the Internet Protocol ("IP"), Transmission Control Protocol ("TCP"), User Datagram Protocol ("UDP"), Hypertext Transfer Protocol ("HTTP"), Hypertext Markup Language ("HTML"), eXtensible Markup Language ("XML") and others.

An operating environment for components of the knowledge system 10 for preferred embodiments of the present invention includes a processing system with one or more high speed Central Processing Unit(s) ("CPU") or other processor(s) and a memory system. In accordance with the practices of persons skilled in the art of computer programming, the present invention is described below with reference to acts and symbolic representations of operations or instructions that are performed by the processing system, unless indicated otherwise. Such acts and operations or instructions are referred to as being "computer-executed," "CPU executed," or "processor executed."

It will be appreciated that acts and symbolically represented operations or instructions include the manipulation of electrical signals by the CPU. An electrical system represents data bits which cause a resulting transformation or reduction of the electrical signals, and the maintenance of data bits at memory locations in a memory system to thereby reconfigure or otherwise alter the CPU's operation, as well as other processing of signals. The memory locations where data bits are maintained are physical locations that have particular electrical, magnetic, optical, or organic properties corresponding to the data bits.

The data bits may also be maintained on a computer readable medium including magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or may be distributed among multiple interconnected cooperating processing systems that may be local or remote to the processing system.

Obtaining Knowledge Based Recommendations with Fused Knowledge

Figure 2:
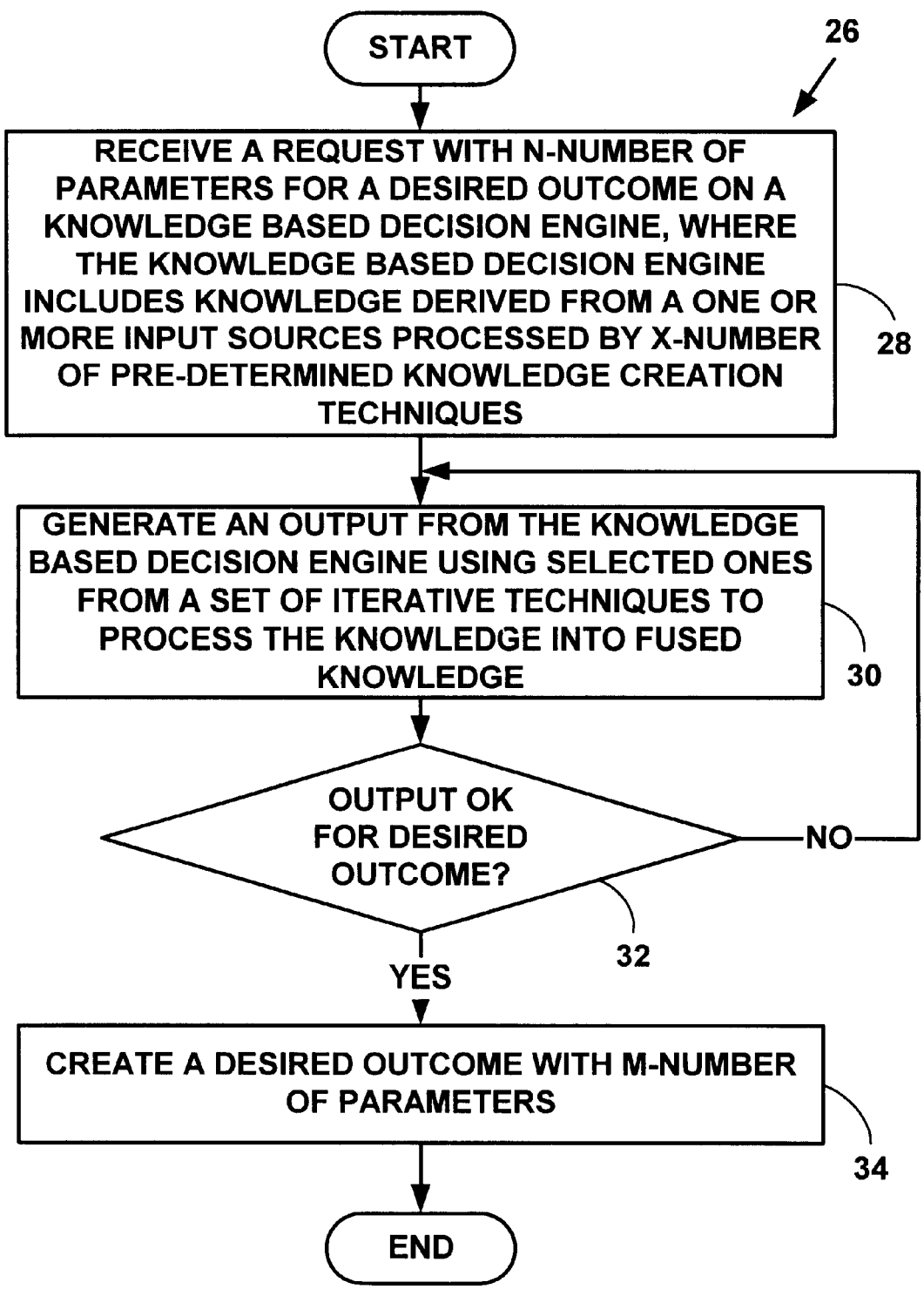
FIG. 2 is a flow diagram illustrating a method for obtaining knowledge based representations.

FIG. 2 is a flow diagram illustrating a Method 26 for obtaining knowledge based recommendations. At Step 28, a request with N-number of parameters is received for a desired outcome on a knowledge based decision engine. The knowledge based decision engine includes knowledge derived from a plurality of input sources processed by X-number of pre-determined knowledge creation techniques. At Step 30, an output is generated from the knowledge based decision engine using selected ones from a set of iterative techniques used to process the knowledge into fused knowledge. At Step 32, a test is conducted to determine if the output is appropriate for the desired outcome. If the output is appropriate for the desired outcome, at Step 34, a desired outcome with M-number of parameters is created. If the output is not appropriate for the desired outcome at Step 32, a loop is entered to repeat steps 30 and 32 until the output is appropriate for the desired result.

Method 26 is illustrated with an exemplary embodiment of the present invention. However, the present invention is not limited to this exemplary embodiment and other equivalent embodiments can also be used.

In such an embodiment at Step 28, a request is received with N-number of parameters for a desired outcome on the knowledge based decision engine 14. For example the request may include a request to get recommendations about a drug candidate compound to synthesize, a drug therapy to test, a virtual drug to develop, etc. A "virtual drug" or "virtual drug compound" is a theoretical drug or compound that has been modeled but not yet actually synthesized. The N-number of parameters may include such parameters as oral availability, desired effects, specific reactions, etc. The N-number of parameters may also be included in a "profile." The profile includes multiple factors ranging from activity at a target site, selectivity, drug absorption, distribution, metabolism and excretion ("ADME") information, toxicology, patient data, etc.

The knowledge based decision engine 14 includes knowledge derived from one or more knowledge data 20 input sources. In one embodiment of the present invention, the knowledge is derived from one or more pharmaceutical information sources or pharmaceutical industry domains including economic, biotech (nucleotide, protein, cell, etc.), chemical, clinical trial, health care provider, reimbursement, sales, pricing, manufacturing, formulation, packaging, screening or other related pharmaceutical industry domains.

Figure 3:
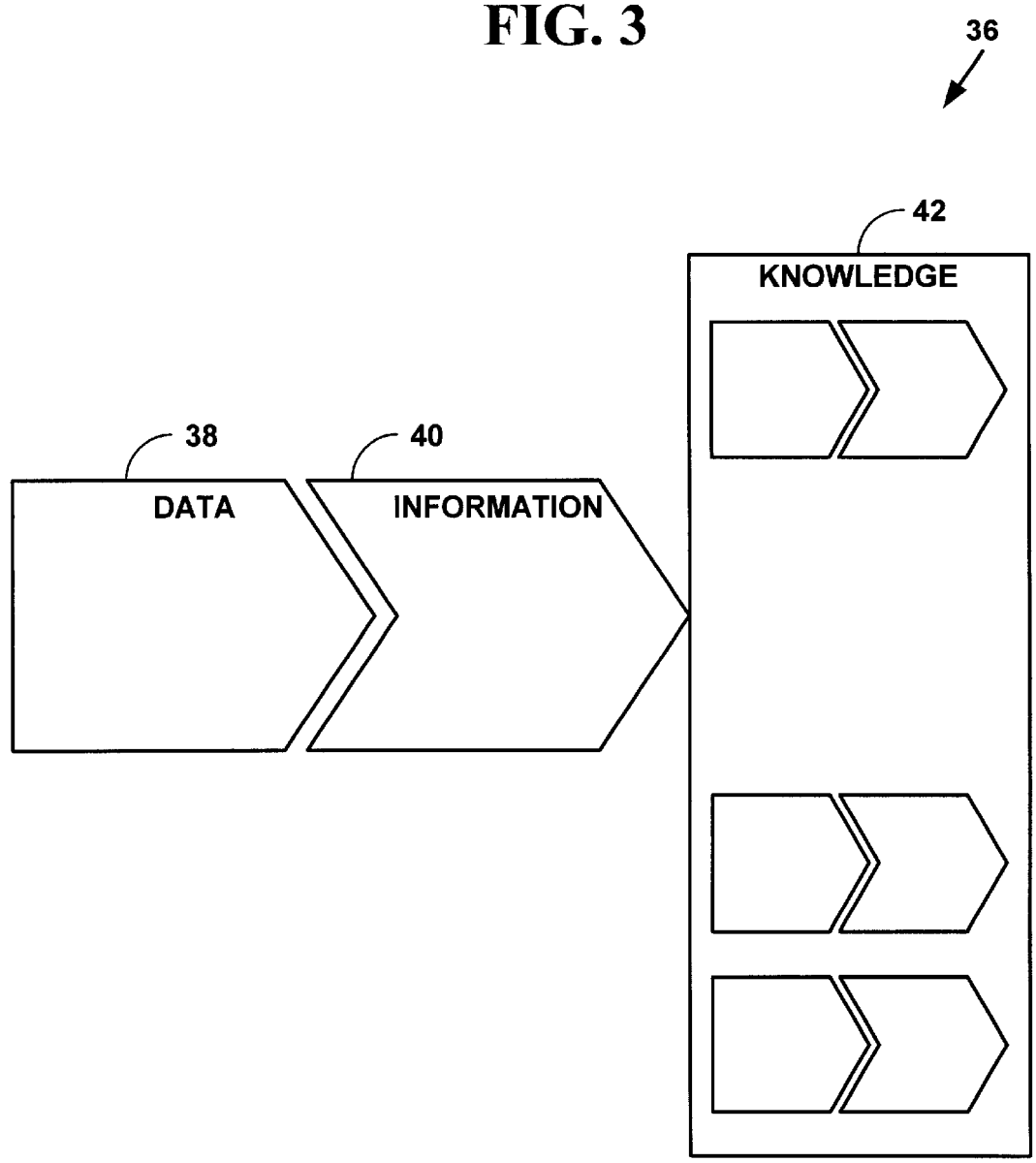
FIG. 3 is a block diagram visually illustrating knowledge.

FIG. 3 is a block diagram visually illustrating derived knowledge 36. Data 38 and information 40 are used to derive knowledge 42. The derived knowledge 42 is derived from the one or more input sources using X-number of knowledge creation techniques that include, but are not limited to, multivariate statistics, genetic algorithm ("GA") techniques, neural network techniques, rule based systems techniques, evolutionary techniques and adaptive techniques. The adaptive techniques may include symbolic, connectionist and hybrid techniques. The evolutionary techniques may include genetic algorithm techniques, genetic programming techniques and spatial genetic algorithms The symbolic techniques include extracting knowledge from a human expert as rules and then placing these into an expertise based system that outputs knowledge. The connectionist approach includes creating expertise based system that comprise many simple processing units connected together and training the whole expertise based system to output knowledge. The connectionist approach has been used to create neural networks of various types to output knowledge. Hybrid approaches include neuro-fuzzy networks that combine rules with neural networks to output knowledge. Such neuro-fuzzy networks cut down search times by initializing an expertise based system with linguistic rules that are then modified in the training process.

Although crossing over into both symbolic and connectionist approaches, an evolutionary approach is typified by genetic algorithm techniques. Genetic algorithms mimic on a computer how actual genes behave in natural selection. Artificial digital genes are constructed of the attributes of interest (e.g., chemical structures for drug 10 s candidates) and rated by classifier rules (e.g., state that certain chemical attributes bind to certain receptor types). A set of classifier rules is termed a "fitness function" and is used to select the genes that survive. Mutation and crossover allow the artificial genes to provide a good solution to a problem over many generations.

Figure 4:
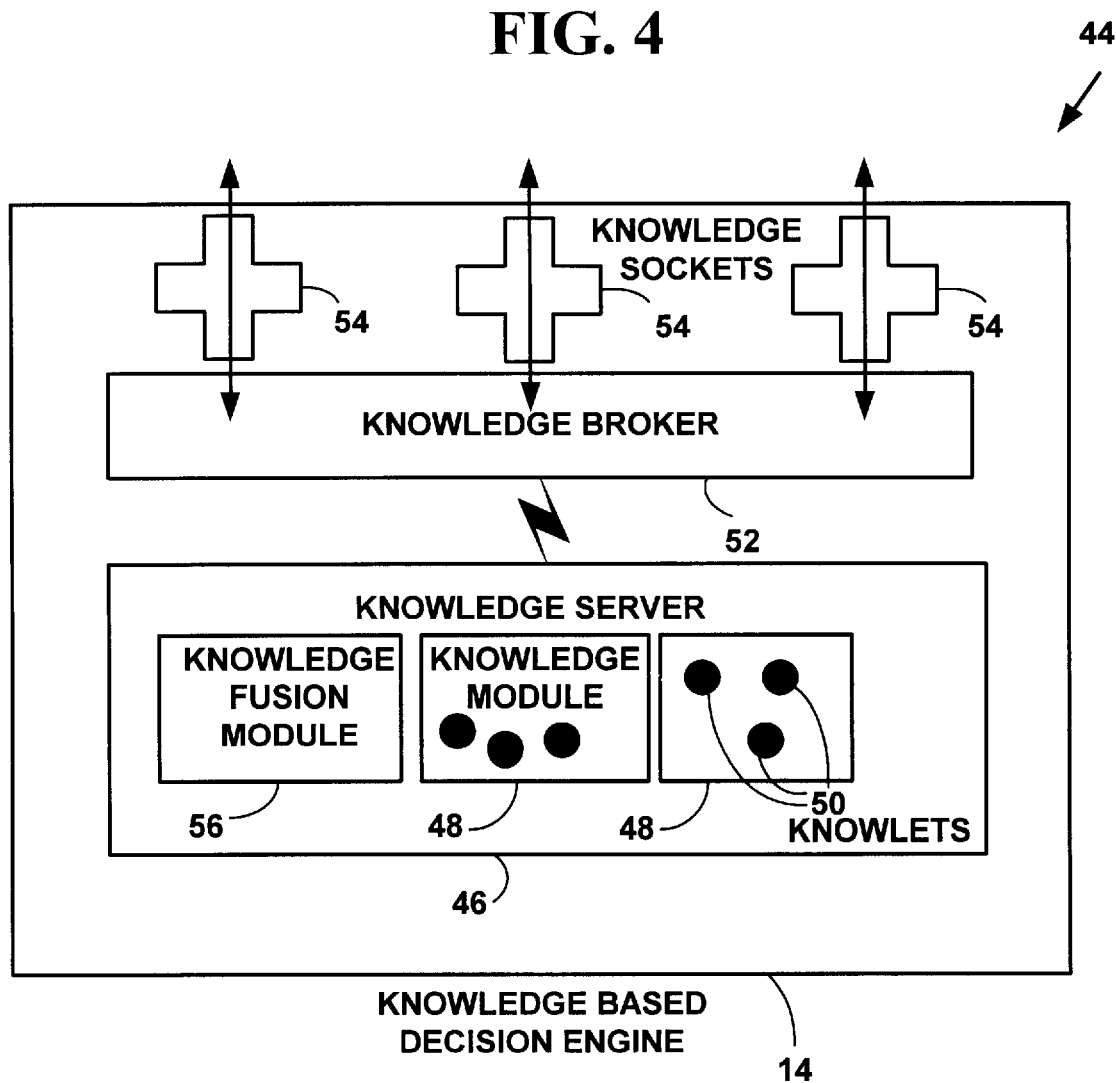
FIG. 4 is a block diagram illustrating exemplary components of a knowledge based decision engine.

FIG. 4 is a block diagram illustrating exemplary components 44 of the knowledge based decision engine 14. In one embodiment of the present invention, the knowledge based decision engine 14 includes a knowledge server 46, multiple knowledge modules 48, multiple knowlets 50, a knowledge broker 52, multiple knowledge sockets 54 and a knowledge fusion module 56. However, the present invention is not limited to these components and the knowledge based decision engine 14 can have more, fewer or equivalent components.

The knowledge server 46 includes self-organizing agents and uses genetic programming methods to deliver the fused knowledge needed to generate high value outputs at Step 30 (FIG. 2). In one embodiment of the present invention, the knowledge server 46 may also include a "Universal Pharma Machine." The Universal Pharma Machine performs the equivalent "operations" of the pharmaceutical industry, i.e., identify new potential drug candidates or therapies, since it is a simulation based on a fusion of appropriate knowledge from all of domains related to the pharmaceutical industry.

A knowledge module 48 fuses knowledge from an individual domain or sub-domain or discipline of one or more industries (e.g., the pharmaceutical industry, etc.) into a queryable object. The queryable object is used with data 38 and information 40 (FIG. 3) to give back knowledge based recommendations as an output at Step 30 (FIG. 2) in order to make decisions for a desired outcome.

The knowledge module 48 uses encapsulation and fusion of knowledge within itself coupled to its queryability to return an output to the knowledge server 46 at Step 30. Individual knowledge modules 48 interact with each other in order to fuse the knowledge from all domains. In one specific exemplary embodiment of the present invention, the knowledge server 46 may comprise only one knowledge module 48, in which case only the knowledge from one individual domain is used to create an output. However, addition of more knowledge modules 48 for more domains will provide better recommendations based on fusion of knowledge, and can include either all available domains or selected domains from multiple industries. As more knowledge modules 48 are added to the knowledge server 46, it delivers more knowledge and is thus able to generate better outputs.

In addition, since an evolutionary and adaptive learning component is also present in the knowledge server 46, it can retain data on how good outputs were arrived at and use this information repeatedly at Steps 30 and 32. The knowledge server 46 hence is not static, but a continually evolving and learning machine, which provides a very powerful decision support capability for producing a desired outcome.

Figure 5:
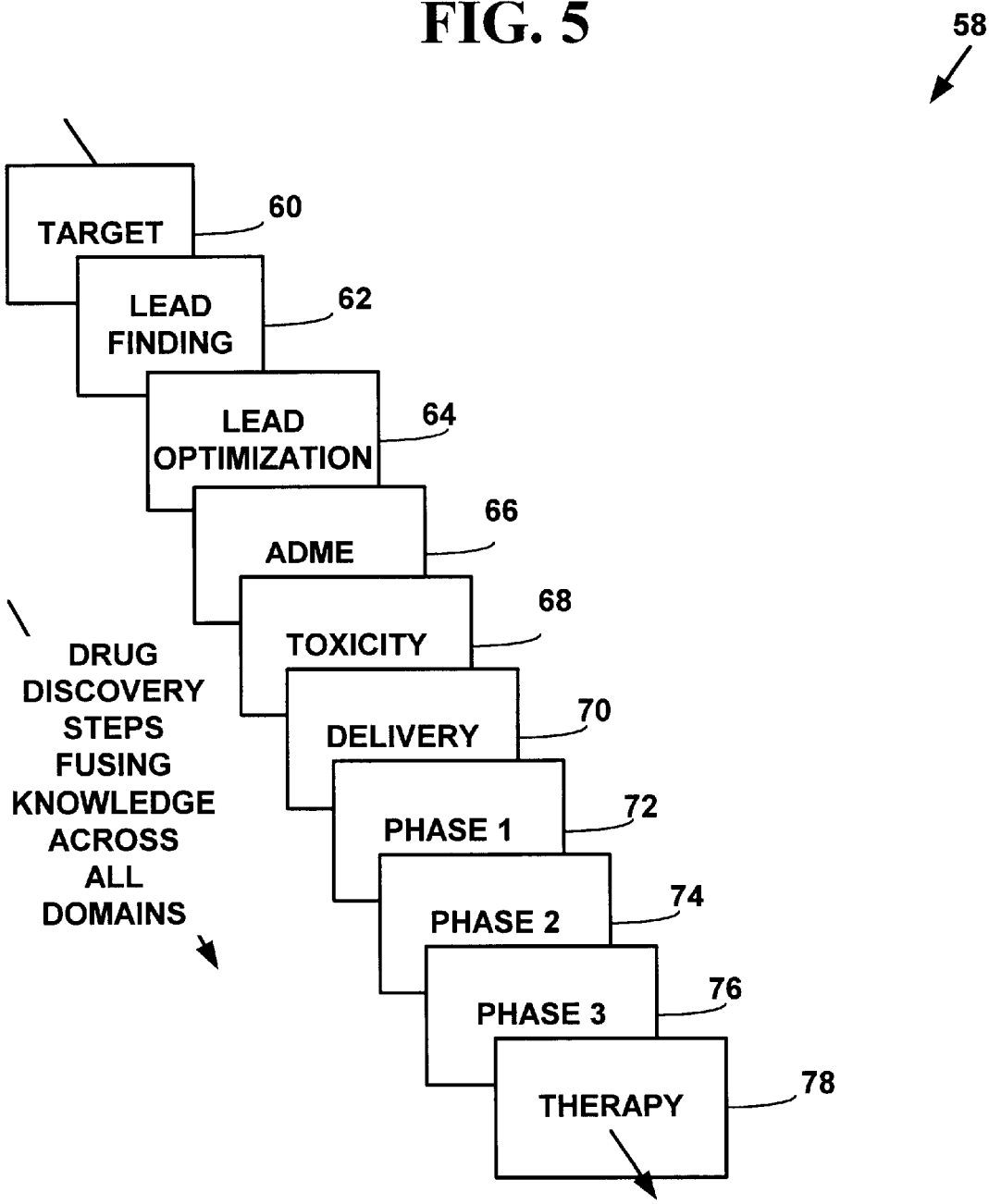
FIG. 5 is a block diagram illustrating exemplary knowledge modules.

FIG. 5 is a block diagram illustrating exemplary knowledge modules 58. FIG. 5 illustrates exemplary drug discovery knowledge modules 60–78 that include domains used in the actual drug discovery process in the pharmaceutical industry. However, the present invention is not limited to drug discovery knowledge modules and virtually any type of knowledge module for virtually any domain from virtually any industry can also be used.

The exemplary drug discover knowledge modules include, for example, a knowledge module for drug candidate targets 60, drug candidate lead finding. 62, drug candidate lead optimization 64, ADME 66, drug toxicity 68, drug delivery 70, phases one, two and three of clinical trials 72, 74, 76, and general public patient therapy 78. Each of these drug discovery knowledge modules includes information from a specific drug discovery domain from the pharmaceutical industry.

Knowledge modules 48,may include one or more knowlets 50. Knowlets 50 may also not be contained within specific knowledge modules 48 but reside in the generality of the knowledge server 46. Knowlets 50 are fundamental "units" of knowledge from a domain or sub-domain from an industry stored in the form of software objects in a knowledge module 48 or within the generality of the knowledge server 46. Knowlets 50 include one or more of the features illustrated in Table 1. However, the present invention is not limited to the knowlet 56 features in Table 1, and more fewer or equivalent features can also be used with knowlets 50.

TABLE 1

- Digital Genes - a knowlet 50 has a digital genetic component to enable it to evolve and this digital genetic component also allows the retention of domain knowledge within the knowlet 50 and the knowlet population. The digital genetic component furthermore allows the knowlet 50 to be given certain basic rules, experience and knowledge at the start of its "life".
- Sensory System - a knowlet 50 has a simple sensory system so that it may "sense" the high level descriptors (see Table 3) used to describe data 38 and information 40 from the domains of an industry (e.g., the pharmaceutical industry).
- Learning - a knowlet 50 has the capability to learn by experience and to retain this learning in a form of memory.
- Basic behavior - a knowlet 50 can be given simple behavioral rules and scenarios to enable it to seek solutions, this behavior can be instantiated genetically (via a genetic program) and reinforced by the learning system. One such example of behavior might be to tell the knowlet 50 the basics of what defines toxic molecules so that it may and learn to recognize them and others based on data from its sensory system. This self organizing approach has advantages over both pure algorithmic methods (e.g., rules etc) or search strategies (e.g., neural networks) by combining knowledge gained from learning experiences of the "environment" and memory. In addition the basic behavior may be learned via a collaborative training with a human expert.

In one embodiment of the present invention, knowlets 50 use a "co-evolutionary" approach. However, the present invention is not limited to a co-evolutionary approach and other approaches can also be used (e.g., symbolic, connectionist, evolutionary, hybrid, etc.). A co-evolutionary approach to knowledge involves the creation of populations of learning entities in a computer environment that allows the entities to succeed at a simple task, thereby allowing the learning entity to evolve with new knowledge obtained from succeeding at the simple task. When they succeed at this task they are allowed to reproduce. Over time the general population of entities gets better at the task and this in turn modifies the environment, such that the population must evolve to get better still. In other words, there is a feedback from the population to the environment and vice versa.

Since the system is based on the relative fitness of competing digital genetic lines there is no need for an absolute fitness function (e.g., used for a GA), instead simplified functions can be used. The co-evolutionary approach thus offers the possibility of evolving behaviors capable of representing real world scenarios inside a created computer environment and then using these environments to play out "games." Games for example, allow an environment try out a desired scenario and recommend the alternatives. This is also known as an "emergent approach" or using emergent behaviors to solve problems.

The co-evolutionary approach has at its core software automata or intelligent software agents. Software agents are self-directed communities of agents given the task of solving certain problems. Already relatively "dumb" self-directed software automata are also solving highly complex problems, by being "programmed" with simple rules and behaviors and then left to evolve. Many popular simulation games use intelligent software agents to provide virtual opponents. Software automata based models such as thermodynamics and weather models are proving very useful modeling at a macroscopic level without having to understand a detailed microscopic level.

This could be considered an anti-reductionist philosophy but in many cases the understanding of the quantum level gives no clues to the macroscopic behavior of a system. Whereas, identification of high level descriptors of systems (e.g., a Mesoscopic level), while effectively ignoring the atomic and molecular level, and instead using intelligent communities of agents, can create understanding of a system far beyond that achievable by quantum methods. In essence complete simulations of systems are created that may then themselves be used to test the outcome of many different scenarios.

A knowlet 50 may therefore include identification of high level descriptors (see Table 3) of all or selected domains and/or sub-domains of an industry, or multiple industries, the encapsulation and fusion as knowledge and the use of that fused knowledge to provide a global model which can then be used to provide optimized outputs at Step 30 (FIG. 2). Exemplary high level descriptors are illustrated in Table 3 below.

The knowlets 50 and the knowlet community use the high level descriptors and fused knowledge already provided by the knowledge modules 48 to allow knowlets 50 to grow, breed and evolve according to basic survival criteria and genetic rules. The survival criteria and generic rules may themselves be derived from knowledge modules 48. It is these rules and survival criteria that allow the knowlets 50 to create a global system model through which different output scenarios are "played" (e.g., drug candidate or therapy scenarios). The knowledge modules 48 and the knowledge server 46 provide the basic environment for the knowlet 50, and its ability to interface with the outside world (e.g., knowledge data 20 and user computer 22) via the knowledge based decision engine 14.

The knowledge broker 52 along with the knowledge server 46 provides an environment for knowledge fusion. The knowledge broker 52 provides a high level resource management function via the organization, integration, interaction and collaboration of the knowledge modules 48 in the knowledge server 46 with the information feed from the data description engine 16 and the knowledge store 12 via a knowledge socket 54. The knowledge broker 52 itself could itself also be composed of the autonomous self-organizing knowlets 50.

The knowledge sockets 54 define and create an infrastructure to pipeline data and information to and from the various knowledge data 20 sources to a knowledge server 46. The knowledge sockets 54 provide an object interface including the features illustrated in Table 2. However, the present invention is not limited to the features in Table 2 and knowledge sockets 54 can have more, fewer or equivalent features.

TABLE 2

- A dynamic object based referencing or wrapping of where appropriate data is and how to manipulate it.
- An interface to data sources via industry standard interfaces (CORBA, JDBC, COM, DCOM, SQL etc.)
- A common interface via an object API to allow the plug in of tools for browsing, query and visualization of data for more traditional analyses which may be of benefit. The analyses performed by these traditional techniques can also be encapsulated into the knowledge server 46.

The knowledge fusion module 56 interacts with the knowledge server 46 and provides basic extraction, encapsulation and knowledge fusion features at Step 30 (FIG. 2).

Figure 6:
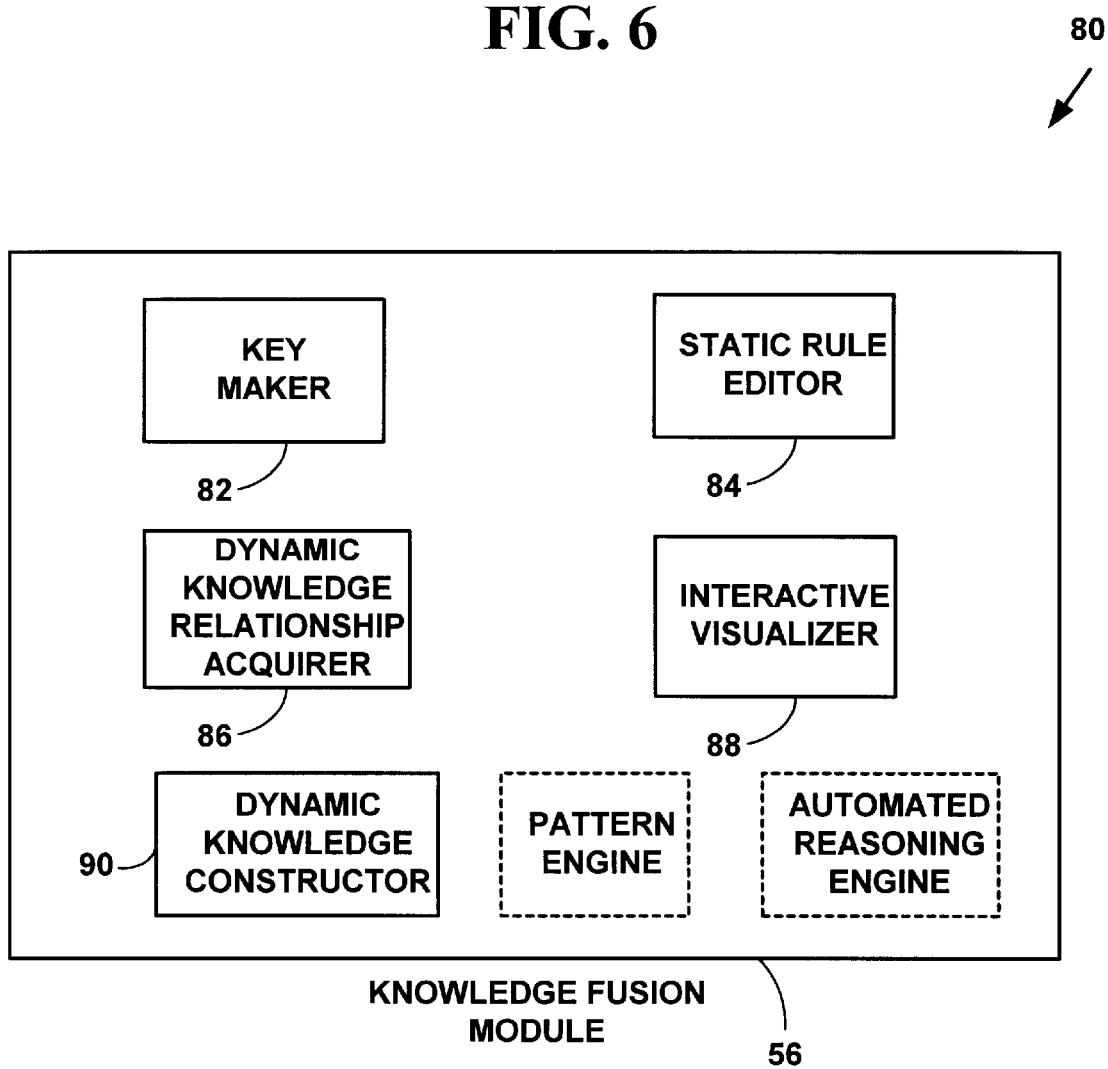
FIG. 6 is a block diagram illustrating exemplary components of a knowledge fusion module.

FIG. 6 is a block diagram illustrating exemplary components 80 of a knowledge fusion module 56. The knowledge fusion module includes a key maker 82, a static rule editor 84, a dynamic knowledge relationship tool 86, an interactive visualizer 88, and a dynamic knowledge constructor 90. The knowledge fusion module 56 may also include a pattern engine (see FIG. 8 and accompanying text) and/or an automated reasoning engine (see FIG. 14 and accompanying text) as described below to further improve creation of fused knowledge. However, the present invention is not limited to such an embodiment and more, fewer or equivalent components can also be used in the knowledge fusion module 56.

The key maker 82 allows the extraction and generation of the knowledge module keys. Knowledge module keys are high order descriptors that are capable of representing the important features in the data and information. Knowledge module keys will be generated, as appropriate, for each domain/sub-domain/discipline/sub-discipline. A knowledge module key may range in complexity from an actual data field from a database, so called meta information (e.g., calculated data) and rules, to simple mathematical models. Knowledge module keys are not static, but are data and result driven. For any particular domain they may change, be replaced or be reduced in their contribution to an overall problem space. This allows the use of an optimum number of optimized descriptors to describe the data and information, and no more, Over-use of descriptors is often a problem with more traditional techniques known in the art.

An example of a proposed set of high level of descriptors is illustrated in Table 3, which illustrates one exemplary set of descriptors used in patient diagnosis and drug therapy. As can be seen from Table 3, very high order descriptors are used. However, the present invention is not limited to the descriptors illustrated in Table 3 and other descriptors can also be used.

TABLE 3

DRUG DISCOVERY/DIAGNOSIS/THERAPY DESCRIPTORS

- Socio-economic
- Presentation to physician (temporal)
- Physical disease symptoms
- Clinical disease symptoms
- Diagnostic tests (invasive and non-invasive)
- Genomic profiles (pharmacogenomics)
- Proteomic profiles (pharmacoproteomics)
- Cell profiles
- Phenotype profiles (pharmacophenomics)

The static rule editor 84 provides rules about data 38 and information 40 used to create knowledge 42. Rules may be fuzzy logic and include mathematical functions. The purpose of this module is to capture knowledge that can be easily expressed linguistically by an expert in a problem domain. Such knowledge is often overlooked or not used with knowledge capture methods known in the art.

The dynamic knowledge relationship acquisition tool 86 extracts what actions a user performed, their order and interrelationships in the analysis schema and a perceived value of each step are used for domain knowledge encapsulation. The result of an analysis in a particular problem domain is only a small part of the knowledge that could be extracted. However, using a variety of both traditional and novel techniques the dynamic knowledge relationship acquisition module 86 captures this type of knowledge.

The interactive visualizer 88 is used for visualization of data. Visualization of data is a very valuable method for extracting patterns that may be transformed into rules about the data, hence aiding the knowledge encapsulation process.

The interactive visualizer 88 provides a set of interactive, drill down views on data, based on both traditional graphing technologies together with the use of domain specific "viewers" to aid users. In addition, as the tool develops, NetMaps and Virtually Reality Markup Language ("VRML") views may be added for highly complex data. In some cases the interactive visualizer 88 may be used at the user interface level (e.g., with GUI 24) to give highly summarized but information rich views linked to one or more knowledge modules 48. The later example in pattern discovery (see FIG. 8) uses this type of approach.

The dynamic knowledge constructor 90 extracts and encapsulates knowledge 42. Much knowledge within and across domains simply cannot be expressed or extracted linguistically or by traditional mathematical models. However this knowledge 42 is inherent in the data 38 and information 40 present. Using "de novo" knowledge construction techniques, it is possible to extract and encapsulate such knowledge directly from the data 38 and information 40 (expressed as knowledge module keys) creating true encapsulated knowledge. Furthermore these techniques permit a linguistic representation in the form of rules, which may be tested and re-edited as appropriate.

Returning to FIG. 2 at Step 32, based on the request at Step 28, the knowledge based decision engine 14 outputs a "best" potential output candidate as fused knowledge at Step 30. At Step 32, a test is conducted to determine determining if the best output is appropriate for the desired outcome. Once the knowledge server 46 has found a best potential output candidate it returns an output based on the request for a desired outcome. The output is fused knowledge and where appropriate will include links to the supportive knowledge on which the output of fused knowledge was generated.

The output and the supportive "drill down" knowledge are used by the knowledge server 46 to make a decision at Step 32. Thus, all the available appropriate knowledge from the individual domains has been fused in parallel and delivered at one decision point at Step 32. The decision at Step 32 includes the ability to use a very wide range of knowledge from different domains of one or more industries, fused together in order to make decisions that are multi-criteria, but made in a single parallel pass rather than done sequentially.

Figure 7:
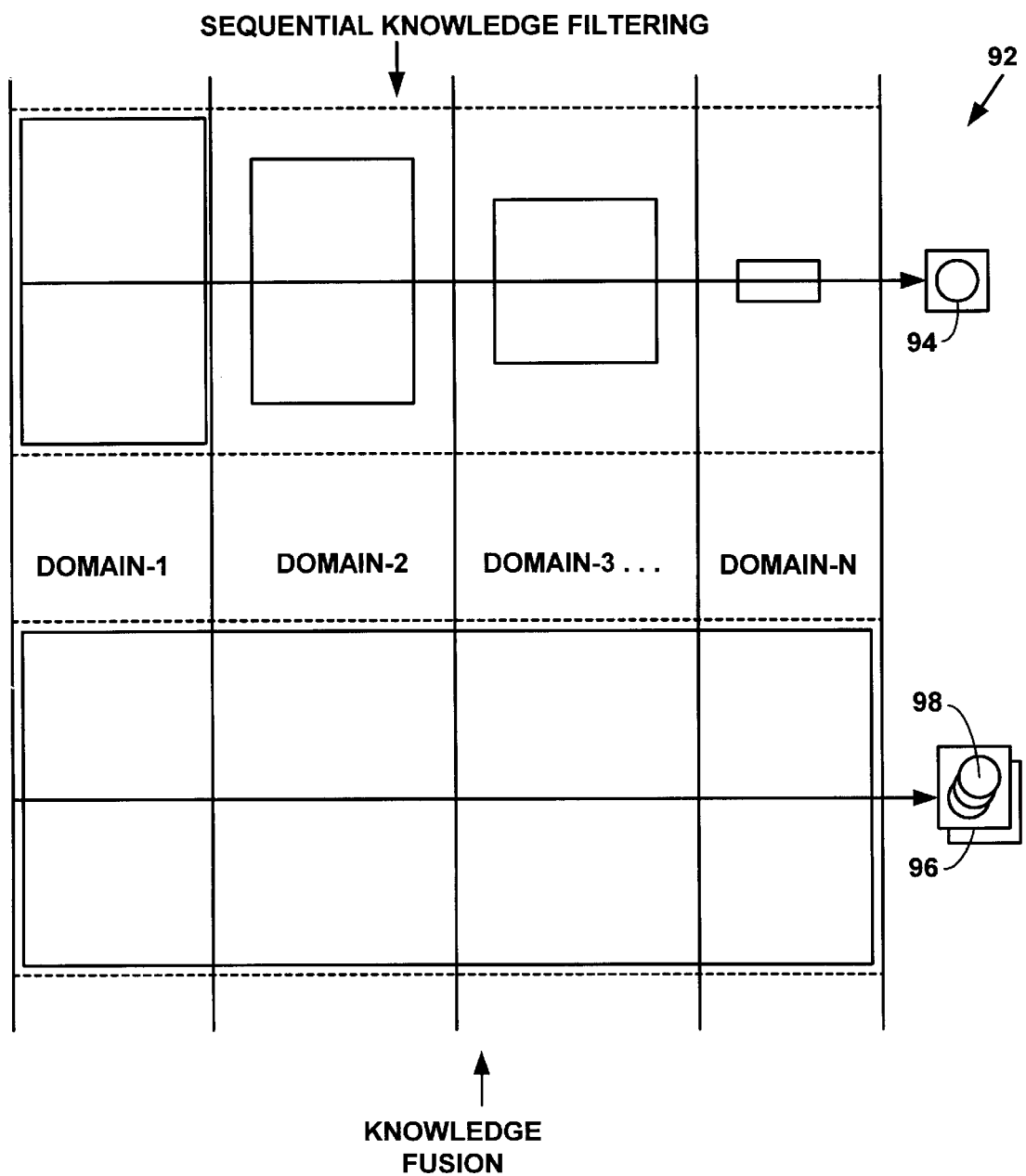
FIG. 7 is a block diagram visually illustrating knowledge gathering.

FIG. 7 is a block diagram visually illustrating knowledge gathering 92. In sequential knowledge gathering techniques known in the art, knowledge is filtered sequentially one domain at a times using only a filtered portion of the available knowledge (illustrated by the dashed lines) in each domain to arrive at an outcome 94. The sequential filtering is illustrated by individual boxes of progressively smaller sizes as only filtered knowledge from an individual domain is considered. When knowledge fusion is used for knowledge gathering, available knowledge from all domains are considered in parallel to arrive at an outcome 96 with multi-criteria 98. The knowledge fusion is illustrated by a box of one size through all of the domains.

The knowledge fusion used is in contrast to the more common domain specific sequential knowledge delivery (or at worst information delivery) systems currently being used in the drug discovery industry, which has resulted in high attrition rates, compounds failing at late stages, reduced pipelines, etc.

If the output is appropriate for the desired outcome, at Step 34, a desired outcome with M-number of parameters is created. The desired outcome includes, for example, a recommendation with multiple parameters including for example, molecular structure, further suggestions, risk assessment, summary explanations, potential therapeutic indications, further information including links to the Internet, an intranet, or other public and private databases, etc.

For example, an exemplary request received at Step 28 for a desired exemplary outcome from the drug discovery industry is illustrated in Table 4. The exemplary request includes three parameters for the desired exemplary outcome for a new drug candidate compound. However, the present invention is not limited to such a request and more or fewer request parameters can also be used.

TABLE 4

Desired outcome - compound 2 specific over compound 1
Input Parameters:

1. Oral availability
2. Reduced gastrointestinal effects over NSAID
3. Enzyme sub-type 2 specific over enzyme sub-type 1

An output including fused knowledge generated at Step 30 is determined to be appropriate for the desired outcome at Step 32. At Step 34, the desired outcome is created with six parameters as is illustrated by the exemplary output in Table 5. However, the present invention is not limited to such an output and more or fewer request parameters can also be used

TABLE 5

Compound 2
Output Parameters:

1. Molecule Structure: (electronic link to graphical representation of chemical structure)
2. Further suggestions: Investigate phenothiazine non-planar ring structures.
3. Risk Assessment: MEDIUM - phenothiazine compounds researched in the 1970's as NSAIDs.
4. Summary Explanation: Phenothiazine ring structure found in a number of anti-inflammatory compounds.
5. Potential Therapeutic Indications: Anti-inflammatory oncology.
6. Further Information: (electronic links to other information)

If the output is not appropriate for the desired outcome, a loop is entered to repeat steps 30 and 32 until a generated output with fused knowledge is appropriate for the desired result In one embodiment of the present invention, the best output is feed back iteratively to the knowledge server 46 and further output generation is requested at Step 30 using the knowledge modules 48 and knowlets 50. Better and better potential outputs are generated using fused knowledge at Step 30 until a generated output is appropriate for the desired outcome at Step 32.

Method 26 and system 10 described herein may be used to provide the following advantages for the pharmaceutical industry; (1) identification of new compounds from virtual libraries or from existing chemical compound libraries; (2) select or predict real or virtual drug compounds in a specific domain with the desired features including, absorption, pharmacokinetics, metabolism, toxicity, clinical decision support, etc.; (3) fusion of knowledge from multiple data, information and knowledge sources (proprietary and public) which incorporates activity and selectivity against a target, desired pharmacokinetic and toxicity properties enabling selection of the compounds from virtual libraries or compound collections which best fulfil desired "drug like" properties; (4) use of existing proprietary and public domain data regarding activity and selectivity at the target site, pharmacokinetics, toxicity, formulation and delivery and clinical outcome to develop a second generation drug which overcomes the current limitations of existing drugs; (5) reduction of the attrition rate among new pharmaceutical candidates accepted for development using knowledge; and (6) provide a horizontal and vertical integration of knowledge across the domains of the pharmaceutical industry business process as distinct from an integration of data and information.

Using Knowledge Data Patterns to Create Fused Knowledge

To reduce the attrition rate among new pharmaceutical candidates, it is desirable to quickly and efficiently recognize patterns representing a desired biological or chemical activity concealed within a range of pharmaceutical data. The desired activity may include activity at a target site, selectivity, ADME, toxicology and other activities.

Figure 8:
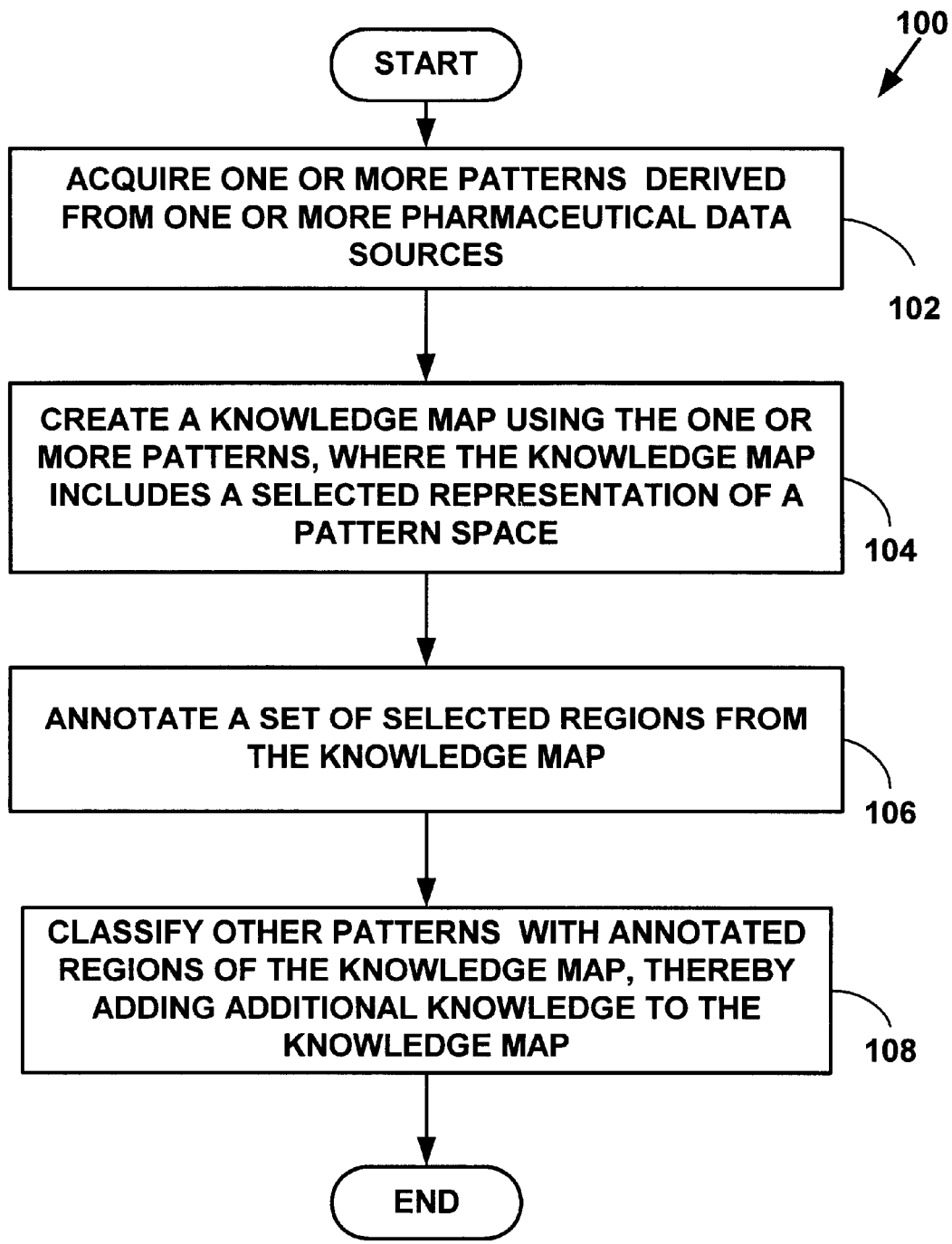
FIG. 8 is a flow diagram illustrating a method for using knowledge data patterns.

FIG. 8 is a flow diagram illustrating a Method 100 for using knowledge data patterns to create fused knowledge. At Step 102, one or more patterns derived from one or more pharmaceutical data sources are acquired. At Step 104, a knowledge map is created using the one or more patterns. The knowledge map includes a selected representation of a pattern space. At Step 106, a set of selected regions from the knowledge map are annotated. At Step 108, other patterns are classified with annotated regions of the knowledge map, thereby adding additional knowledge to the knowledge map.

Method 100 may used within the knowledge based decision engine 14 to improve creation of fused knowledge. Specifically, Method 100 may be used within the knowledge fusion module 56 as a pattern engine (see FIG. 6) to locate and describe previously unrecognized patterns of biological activity concealed within a range of drug discovery data.

Method 100 is illustrated with an exemplary embodiment of the present invention for drug discovery. However, the present invention is not limited to this exemplary embodiment and other equivalent embodiments can also be used for other purposes.

At Step 102, one or more patterns derived from one or more pharmaceutical data sources are acquired. The patterns are cluster patterns from screening of biological or chemical data for the purpose of classifying drug discovery data. In one embodiment of the present invention, the cluster patterns are derived with the co-evolutionary techniques described above. However, the present invention is not limited to cluster patterns derived from co-evolutionary techniques.

Figure 9:
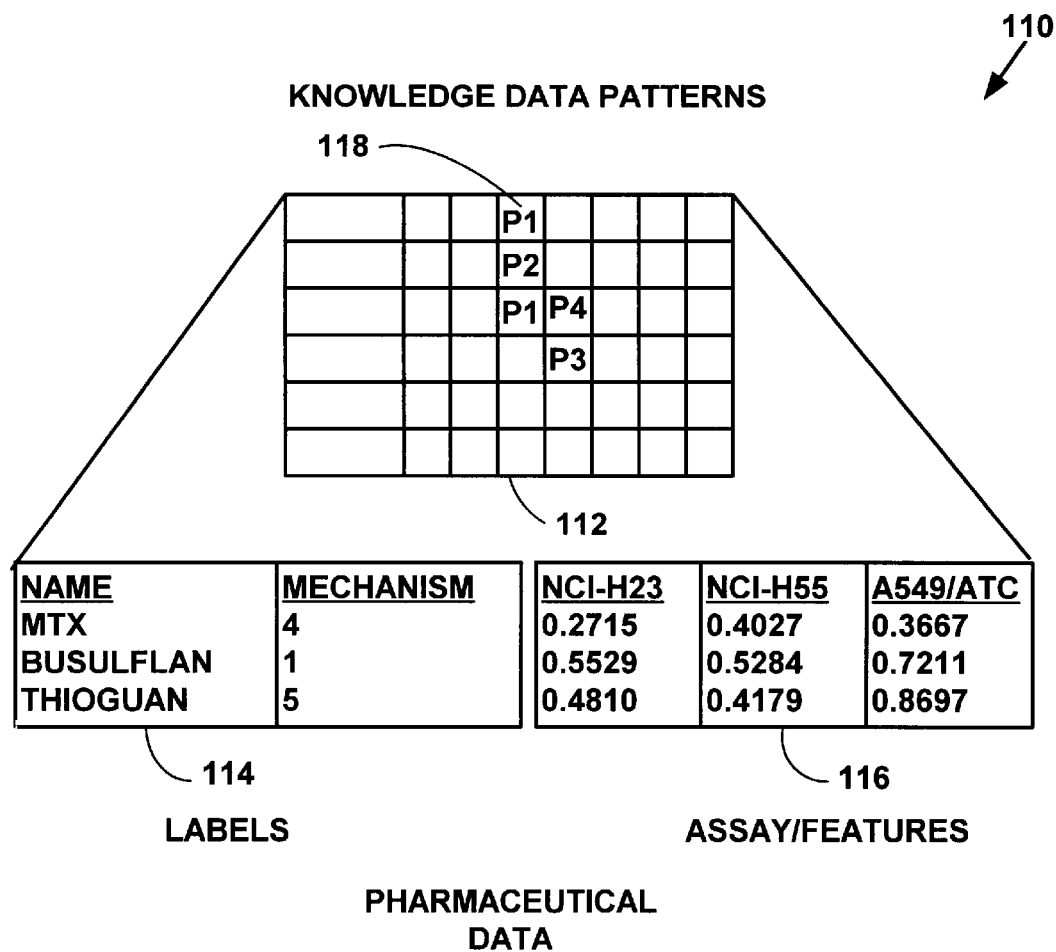
FIG. 9 is a block diagram illustrating a knowledge data pattern.

FIG. 9 is a block diagram illustrating an exemplary knowledge data pattern 110. One more patterns 112 (illustrated by Px, where x is a pattern from the set {1, 2, 3, ...}) are obtained from sets of drug discovery screening data 114 and a set of assays or features 116. As is known in the art, an "assay" is a specific implementation of data processing methods used to analyze data and return results related to biological or chemical processes being examined.

For example, a "cell assay" is a specific implementation of image processing methods used to analyze images and return results related to biological processes being examined. As is known in the art, a "cell protocol" specifies a series of system settings including a type of analysis instrument, a cell assay, dyes used to measure biological markers in cells, cell identification parameters and other general image processing parameters used to collect cell data.

Using image processing methods, the "size" of an object can be represented by its area, perimeter, boundary definition, length, width, etc. The "shape" of an object can be represented by its rectangularity (e.g., length and width aspect ratio), circularity (e.g., perimeter squared divided by area, bounding box, etc.), moment of inertia, differential chain code, Fourier descriptors, etc. The "intensity" of an object can be represented by a summed average, maximum or minimum grey levels of pixels in an object, etc. The "texture" of an object quantifies a characteristic of grey-level variation within an object and can be represented by statistical features including standard deviation, variance, skewness, kurtosis and by spectral and structural features, etc. The "location" of an object can be represented by an object's center of mass, horizontal and vertical extents. etc. with respect to a pre-determined grid system.

For more information on digital image feature measurements, see: "Digital Image Processing," by Kenneth R. Castleman. Prentice-Hall, 1996, ISBN-0132114674, "Digital Image Processing: Principles and Applications," by G. A. Baxes, Wiley, 1994, ISBN-0471009490, "Digital Image Processing," by William K. Pratt, Wiley and Sons, 1991, ISBN-0471857661, or "The Image Processing Handbook—$2^{nd}$ Edition," by John C. Russ, CRC Press, 1991, ISBN-0849325161, the contents of all of which are incorporated by reference.

The drug discovery screening data patterns include patterns of biological and chemical activity concealed within a range of drug discovery data. The patterns are used to classify drug discovery data. The patterns include, for example, toxicity patterns 118, absorption, distribution, metabolism or excretion patterns, digital image analysis patterns, etc.

Returning to FIG. 8 at Step 104, a knowledge map is created using the one or more patterns. The knowledge map includes knowledge for, a new real or virtual drug compounds or drug therapy. In one embodiment of the present invention, the knowledge map is generated from cluster patterns (e.g., P1 118) from drug screening data using a self-organizing map for the purpose of classifying drug discovery data. As is known in the art, "self-organizing maps" utilize neural network methodologies to group any hidden or previously unknown patterns underlying a given data set.

Self-Organizing maps or "Kohonen networks" are a subset of the computer learning methodology known as "neural networks." For more information on self-organizing maps see, "Self-Organizing Maps", by Teuvo Kohonen, Springer Series in Information Sciences, Vol. 30, Springer-Verlag, Berlin, Germany, 1995,. ASIN-3540586008, the contents of which are incorporated herein by reference. As is known in the art, a neural network is a network of many simple processors, units, connected by communication channels, that carry data. The units operate only on their local data and on the inputs they receive via the connections. Neural networks have a "training" rule whereby the weights of connections are adjusted on the basis of data. By this means neural networks "learn" from examples.

Figure 10:
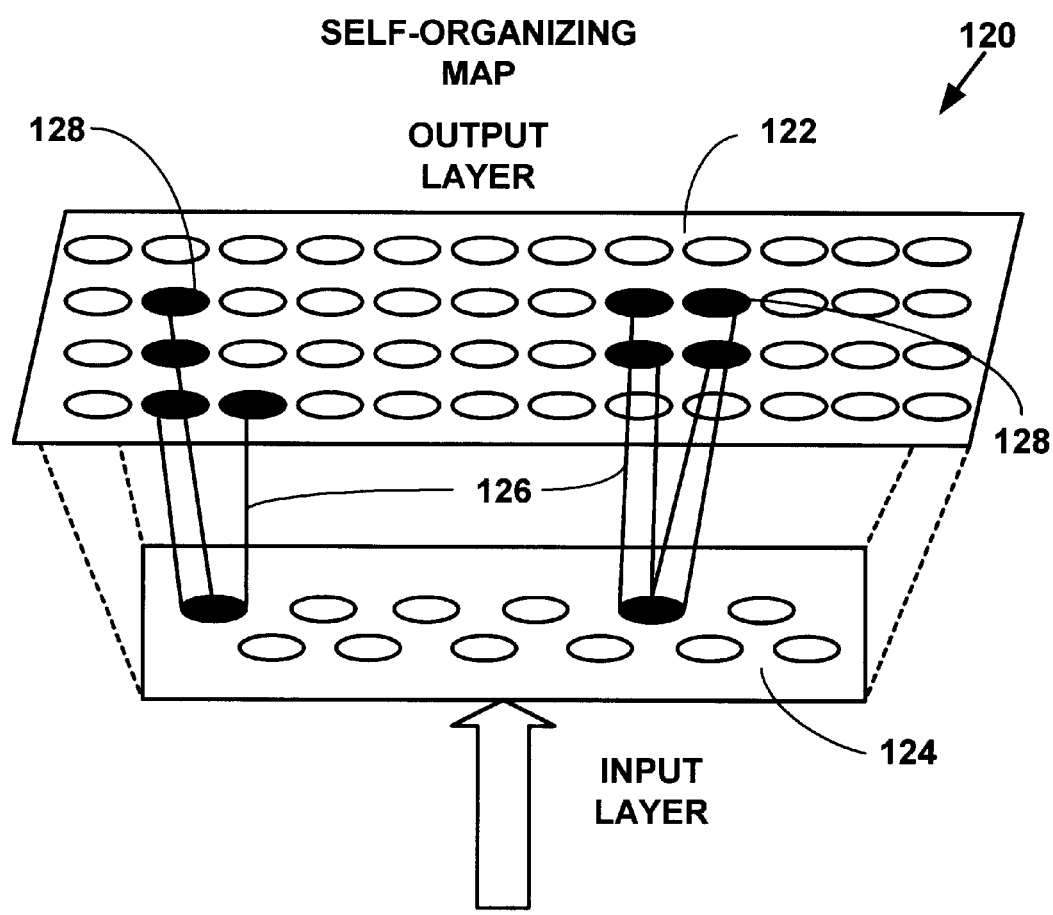
FIG. 10 is a block diagram illustrating a self-organizing map.

FIG. 10 is a block diagram illustrating an exemplary self-organizing map 120. The self-organizing map includes a single two-dimensional output layer 122 of units and an input layer 124 that corresponds to input data. There is a link between output nodes in the output layer 122 and input nodes in the input layer 124. During training, weights of connections are altered in such a way as create associations 126 between the input nodes and the output nodes. This association creates clusters of units 128 that correspond to different classes (with statistically similar properties) that are present in the training data.

A self-organizing map 120 is particularly suited to the analysis of drug discovery data where it is necessary to analyze a large number of examples and identify groups with similar features. A map of input data produced by the self-organizing map 120 is non-linear and is typically much richer and more robust than those provided by conventional pattern recognition methods used for drug discovery known in the art.

Figure 11:
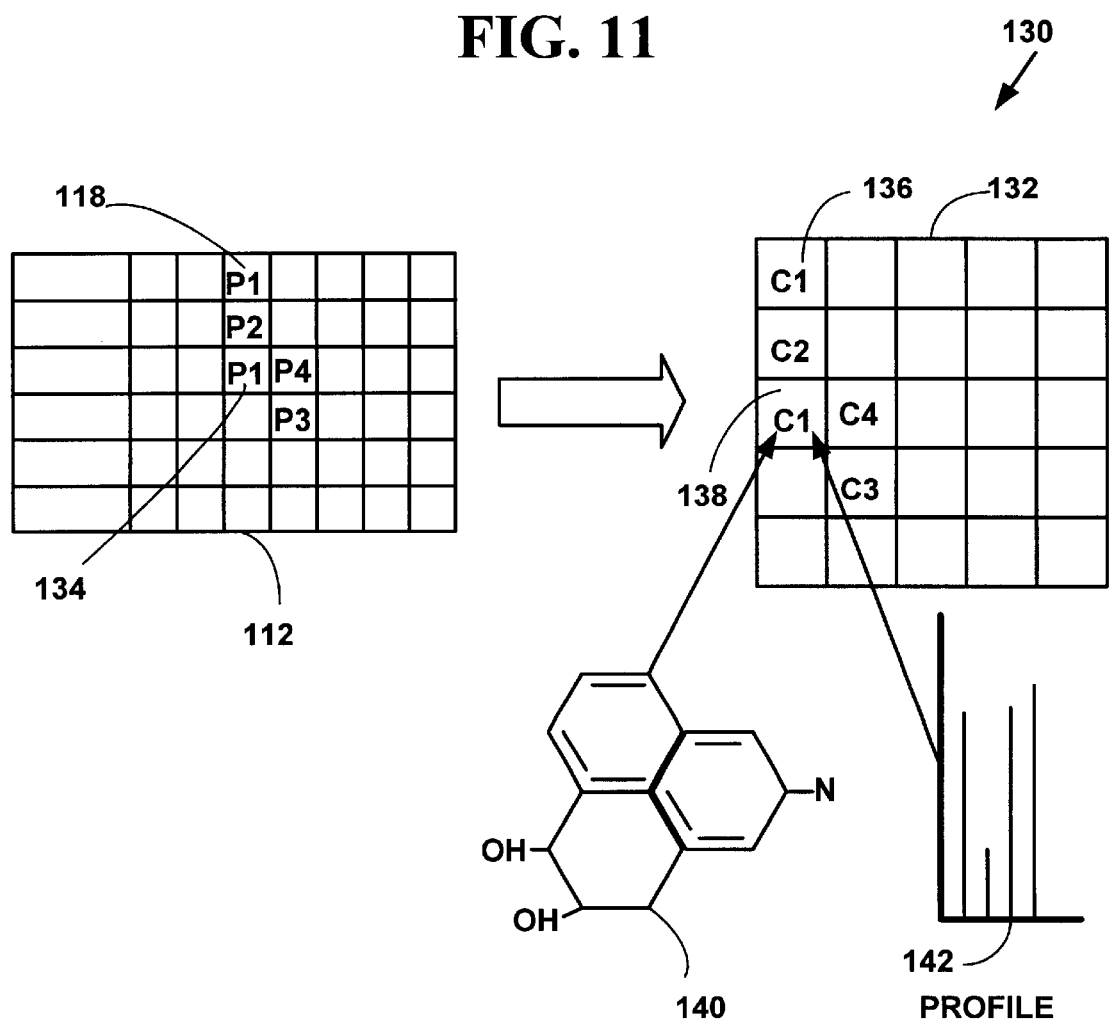
FIG. 11 is a block diagram illustrating a visual representation of a self-organizing map.

FIG. 11 is a block diagram illustrating a visual representation 130 of a knowledge map 120. A visual knowledge map 132 relates patterns (e.g., P1) 118, 134 that are similar to a region 136, 138 (e.g., nodes) on the map providing topological preservation. This is visually illustrated by using the same colors (e.g., C1=P1, C2=P2, etc.) for the nodes on the map. Multiple colors are used to allow a manager, analyst or researcher to determine common patterns in an easier and more efficient manner. The visual knowledge map 132 may be displayed on GUI 24.

Returning to FIG. 8 at Step 106, a set of selected regions from the knowledge map 112 are annotated. The set of selected regions from the knowledge map are preferably automatically annotated using knowledge from the knowledge store 12 or with fused knowledge created with Method 26 (FIG. 2). However, the set of selected regions from the knowledge map can also be annotated manually by human analysts or researchers.

The visual knowledge map 132 is used to illustrate such annotation. However, a non-visual knowledge map can also be annotated. Labels 114 (FIG. 9) text and other data (e.g., chemical structures 140 and biological profiles 142, etc. FIG. 11) from the original data are then used to annotate the selected regions (e.g., 136, 138) of the visual knowledge map 132 (FIG. 11). The annotated set of selected regions can also be opened and explored, drilling down to other data (e.g. 140, 142, FIG. 11), to "explain" the pattern groupings.

At Step 108, other patterns are classified with annotated regions of the visual knowledge map 132, thereby adding additional knowledge to the visual knowledge map 132. The other patterns can be other known patterns for known chemical compounds or other new patterns for unknown chemical compounds.

In one embodiment of the present invention, an unknown pattern is optionally recognized as a "familiar pattern" by comparing the unknown pattern with known annotated patterns on the knowledge map. The unknown pattern is optionally annotated as a familiar pattern. A familiar pattern may represent a yet unknown compound that exhibits familiar characteristics to known compounds.

In one embodiment of the present invention, at Step 108, one or more groups of similar patterns are created. An unknown pattern is added to a group to which the unknown pattern it closest to in the pattern space. Groups of patterns may be used to group compounds with similar characteristics or responses.

Figure 12:
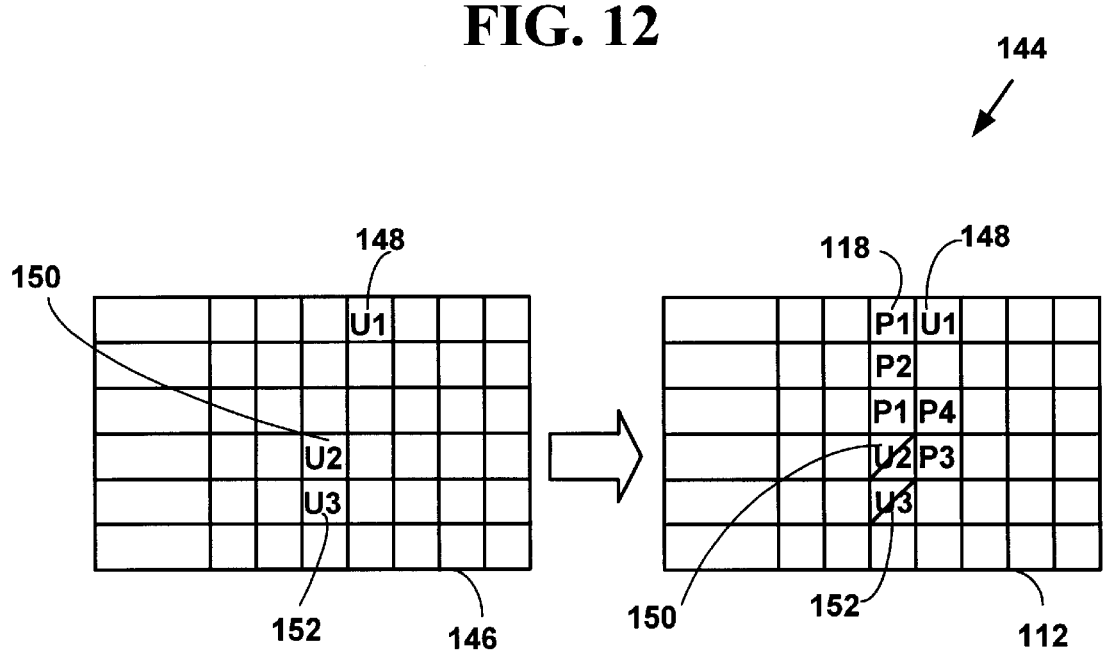
FIG. 12 is a block diagram illustrating classifying other patterns on a knowledge map.

FIG. 12 is a block diagram 144 visually illustrating other patterns on a knowledge map 112 (FIG. 9). A set of unknown assays/features 146 includes individual unknown assays/features U1, U2 and U3 148, 150, 152. These unknown assays/features are determined from an unknown candidate drug compound that was tested during drug discovery screening experiments. The unknown patterns U1–U3 are presented to the knowledge map 112, to see how they match. Distances or other measurements between unknown patterns and known patterns in the selected regions of the knowledge map are measured. When a distance measurement or other measurement falls within a pre-determined tolerance, other patterns are classified, thereby adding additional knowledge to the knowledge map 112.

For example, unknown pattern U1 148 (FIG. 12) falls within the pre-determined tolerance and can be classified with pattern P1 118, thereby adding addition knowledge to the knowledge map 112. In contrast, unknown patterns U2 150 and U3 152 are too far away from patterns P2 and P3 (FIG. 12), and do not fall within the pre-determined tolerance. Thus, these unknown patterns U2 and U3 150, 152 cannot be classified at this instance of time. However, as additional knowledge is added to the knowledge map 112, unknown patterns U2 and U3 150, 152 may eventually be classified.

Assay or feature data of members of the unknown patterns U1–U3 150–154 could also be used to create a "virtual assay" or predict "virtual features" for unknown compounds, without actually knowing what the unknown compounds are, or understanding how the unknown compounds may actually function. Thus, a virtual assay or virtual features can also be validated using a final outcome without intermediate understandings via Method 100.

Figure 13:
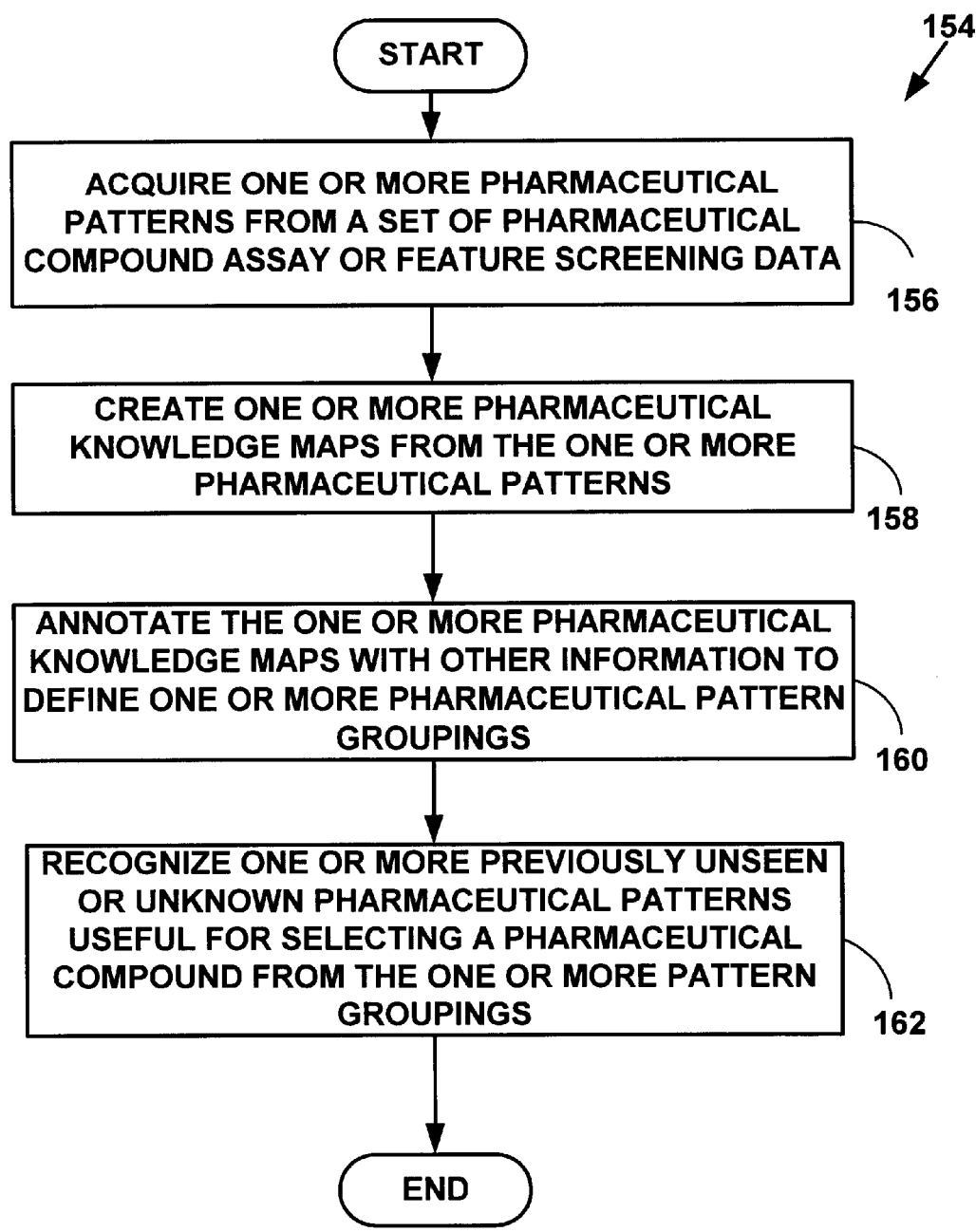
FIG. 13 is a flow diagram illustrating a method for creating and using knowledge maps to determine pharmaceutical compounds.

FIG. 13 is a flow diagram illustrating a Method 154 for creating and using knowledge maps to determine pharmaceutical compounds. At Step 156, one or more pharmaceutical patterns are acquired from a set of pharmaceutical compound assay or feature screening data. At Step 158, one or pharmaceutical knowledge maps are created from the one or pharmaceutical patterns. At Step 160, the one or more pharmaceutical knowledge maps are annotated with other information to define one or more pharmaceutical pattern groupings. At Step 162, one or more previously unseen or known pharmaceutical patterns are recognized from the one or more pharmaceutical pattern groupings, thereby creating new pattern grouping knowledge useful for selecting a pharmaceutical compound.

Method 154 is illustrated with an exemplary embodiment of the present invention for drug discovery. However, the present invention is not limited to this exemplary embodiment and other equivalent embodiments can also be used for other purposes.

At Step 156, one or more pharmaceutical patterns are acquired from a set of pharmaceutical compound assay or feature screening data (toxicity patterns, ADME patterns, etc.). In preferred embodiments of the present invention, pharmaceutical patterns include information obtained from biological systems, biological processes, biochemical processes, biophysical processes, chemical processes, pharmaceutical processes, drug discovery processes, economic processes clinical trial processes, health care provider processes, reimbursement processes, sales processes, pricing processes, manufacturing processes, formulation processes, packaging processes, screening processes or other processes.

At Step 158, one or pharmaceutical knowledge maps are created from the one or pharmaceutical patterns. Pattern based pharmaceutical knowledge maps are created using self-organizing maps as is described above.

At Step 160, the one or more pharmaceutical knowledge maps are annotated with other information to define one or more pharmaceutical pattern groupings. The annotation of these pharmaceutical knowledge maps with other information defines pharmaceutical pattern groupings with similar features (e.g., similar mechanisms of action, activity levels, etc.). The pharmaceutical knowledge maps include knowledge for a real or virtual drug compound or drug therapy.

At Step 162, one or more previously unseen or unknown pharmaceutical patterns are recognized from the one or more pattern groupings. Previously unseen or known pharmaceutical patterns are mapped to the known and annotated pattern groupings, thereby creating new pattern grouping knowledge useful for selecting a new real or virtual pharmaceutical compound or creating a new real or virtual drug therapy. In one embodiment of the present invention, Step 162 includes adding an unknown pattern to a pharmaceutical pattern grouping to which the unknown pattern closest to in a pattern space used to define the pharmaceutical knowledge map (e.g., pattern space for a self-organizing map).

Methods 100 and 154 may, be used to provide the following advantages for the pharmaceutical industry: (1) the ability to look for undiscovered trends via pattern analysis in large amounts of data in an automated manner, that could not easily be done manually by human researchers or analysts; (2) automatically search large amounts of data (e.g., terabytes of data) for existing new or previously unknown patterns; (3) obtaining new knowledge about a process or compound to further improve the process or compound; (4) may be very useful (if used wisely) in conjunction with screening and drug discovery data, to create "filters" of data that are outcome driven (i.e., no need to actually understand all aspects of filtered data); and (5) improve creation of fused knowledge for drug discovery and other industry processes.

Using Automated Reasoning to Improve Fused Knowledge

To reduce the attrition rate among new pharmaceutical candidates it is also desirable to remove common data errors. When automated screening systems are used there are almost always common screening "problems" primarily associated with finding patterns on assay microplates that relate to pipetter errors (e.g., a clogged or partially clogged pipetter head), common microplate preparation errors, microplate variances within runs, bio chip errors, gel-electrophoresis errors, etc. In short, errors related to a "physical experimental environment" occur rather than the "biological specific" errors. It is desirable to remove such physical errors and others to improve interpretation and validation-of any fused knowledge that is created. However, "biological-specific errors" such as errors in assays can also occur. It is also desirable to remove biological specific errors when possible to improve fused knowledge.

Figure 14:
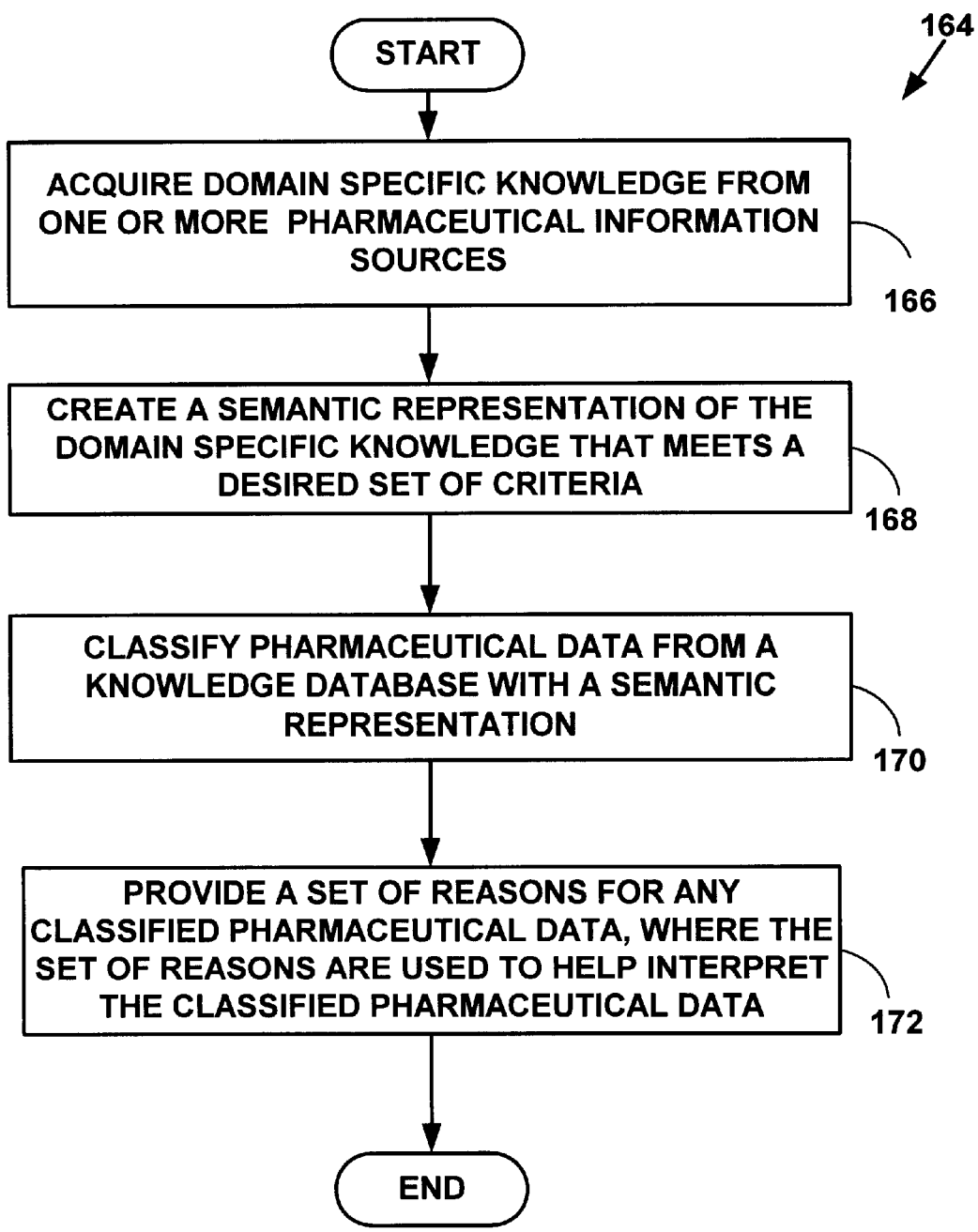
FIG. 14 is a flow diagram illustrating a method for interpreting experimental data with automated reasoning.

FIG. 14 is a flow diagram illustrating a Method 164 for interpreting and validating experimental data with automated reasoning. At Step 166, domain specific knowledge is acquired from one or more pharmaceutical information sources. At Step 168, a semantic representation of the domain specific knowledge is created that meets a desired set of criteria. At Step 170, pharmaceutical data from a knowledge database is classified with a semantic representation. At Step 172, a set of reasons is provided for any classified pharmaceutical data. The set of reasons are used to help interpret the classified pharmaceutical data and create fused knowledge from the pharmaceutical data.

Method 164 may be used within the knowledge based decision engine 14 to improve creation of fused knowledge. Specifically, Method 164 is preferably used as an automated reasoning engine (see FIG. 6) within the knowledge fusion module 56 to locate and describe previously unrecognized patterns of error activity concealed within a range of drug discovery data. However, in a less preferred embodiment or the present invention, the set of reasons can be manually provided by human analysts or researchers.

Method 164 is illustrated with an exemplary embodiment of the present invention for drug discovery. However, the present invention is not limited to this exemplary embodiment and other equivalent embodiments can also be used for other purposes.

In such an embodiment, at Step 166, domain specific knowledge is acquired from one or more pharmaceutical information sources. The pharmaceutical industry domains including economic, biotech (nucleotide, protein, cell, etc.), chemical, clinical trial, health care provider, reimbursement, sales, pricing, manufacturing, formulation, packaging, screening or other related pharmaceutical industry domains.

At Step 168, a semantic representation of the domain specific knowledge is created from the knowledge store 12 that meets a desired set of criteria using high level descriptors (e.g., from Table 3). As was described above, a semantic representation includes applying relationships between words or symbols and their intended meanings and to represent relationships among objects, ideas, or situations with a set of rules.

In one embodiment of the present invention, the semantic representation includes a semantic representation of a general screening expert, an instrument expert, an assay expert, and many other experts from pharmaceutical industry domains. Such semantic representations include a specified set of rules. However, the present invention is not limited to these specific semantic representations, and more, fewer or equivalent semantic representations can also be used.

For example, a semantic representation of a general screening expert includes a set of rules for entities such as microplates, with wells, fields and other microplate features, bio-chips, etc. Collecting data from a microplate used for screening typically includes 96 to 1536 or more individual wells. As is known in the art, a "microplate" is a flat, shallow dish that stores multiple samples for analysis. A "well" is a small area in a microplate used to Include an individual sample for analysis. Each well may be divided into multiple fields. A "field" is a sub-region of a well that represents a field of vision (i.e., a zoom level) for a photographic microscope. Each well is typically divided into one to sixteen fields. A "feature" is a measurement made in a field.

As is known in the art, a "bio-chip" is a stratum with hundreds or thousands of absorbent individual "containers" (e.g., micro-wells, micro-gels, other compounds, etc.) fixed to its surface. A single bio-chip may include 10,000 or more individual containers. When performing an assay test, each container on a bio-chip is like a micro-test tube or a well in a microplate. A bio-chip provides a medium for analyzing known and unknown biological (e.g., nucleotides, cells, etc.) samples in an automated, high-throughput screening system. Various types of gels may also be used with a gel-electrophoresis processes to collect nucleotide and other types of genome data.

A semantic representation of a general screening expert may include, for example, semantic relationships for bio-chips, microplates, wells in a microplate, fields in a well (e.g., individual features of an object of interest such as a nucleotide sequence, a cell, etc.) summary features in a well (e.g., statistical features, instrument summary features, etc.) and other types of semantic relationships.

Table 6 illustrates exemplary general screening, instrument and assay software experts with specific functionality that is used to create a semantic representations.

However, the present invention is not limited to the expert functionality in Table 6, and additional, fewer or equivalent software experts with virtually any other type of functionality can also be used.

TABLE 6

1. General Screening Expert - The basic functionality of this expert is common screening "problems" primarily to do with finding patterns on assay microplates that relate to pipetter errors, common microplate preparation errors microplate variances within runs bio-chip errors, gel-electrophoresis errors, etc. In short the "physical" errors that occur rather than the "biological" (e.g., assay specific errors).
2. Instrument Expert - The basic functionality of this expert is related to gross identifiable problems in an instrument (i.e., are relevant to data not yet propagated). Different instrument experts are created for different instrument manufacturers.
3. Assay Expert - The basic functionality of the expert is related to identifiable biological specific problems of a biological assay. This expert is based on knowledge encoded into rules for general assay types (e.g., nucleotide processing, ligand binding, cell based, etc.)

At Step 170, pharmaceutical data 20 from the knowledge store 12, is classified with semantic representation. In one embodiment of the present invention, the semantic representation is used to identify clusters of activity found on individual assay microplates and from this determine the current behavior of instrumentation (e.g., a pippeting robot). Assay specific information is classified that-will transfer knowledge gained in assay development to the screening process so as to greatly enhance the discovery, validation and verification of lead pharmaceutical candidates.

For example, a semantic representation of a general screening expert or instrument expert is applied to a set of pharmaceutical data to find patterns on assay microplates that relate to "physical" errors that occur such as pipetter errors, common microplate preparation errors and microplate variances within screening runs. A semantic representation of an assay expert is applied to find patterns on assay microplates that relate to "biological" errors that occur in an assay.

In one embodiment of the present invention, Step 170 includes applying a set of heuristics to determining whether any of the pharmaceutical data meets a desired set of criteria. The set of heuristics, include but are not limited to, heuristics coded into specific rules that are used to classify pharmaceutical data via semantic representations.

At Step 172, a set of reasons is provided for any classified pharmaceutical data. The set of reasons are used to help interpret the classified pharmaceutical data and create better fused knowledge from the pharmaceutical data. For example, the set of reasons may include such reasons as "You have a suspect block of six hits in assay 1001 in microplate 390. This possibly a clogged pippet error."

Since the errors in this example are "physical" errors rather than the "biological" errors, such physical errors can be identified and classified as such. Such physical error classified pharmaceutical data can then be marked as unreliable data or removed from the knowledge store 12 altogether before fused knowledge is created at Step 30 (FIG. 2), thereby improving any fused knowledge created.

Biological specific errors can be classified in a similar manner. Such biological specific error classified pharmaceutical data can also be marked as unreliable.

FIG. 15 is a block diagram visually illustrating exemplary output. 174 from Method 164. The output 174 illustrates a data summary section 176 including information such as a pharmaceutical data block identifier, hit number, microplate number, assay number, an X-position (e.g., 1–12) and Y-position (e.g., A–H) in a microplate and a pharmaceutical compound identifier. The output 174 also includes a graphical representation of multiple wells 178 in a microplate (i.e., 12×8=96 wells). Hits indicating pharmaceutical data with physical errors are visually indicated with an "H" 180 on the graphical representation of the microplate. The output also includes a report section 182 that includes a set of reasons is provided for any physical error classified pharmaceutical data. The output 174 may also be used in a similar manner for biological specific errors The graphical representation of multiple wells 178 in the output 174 is not limited to microplates of 96 wells (or 8 rows by 12 columns) and may be used to represent microplates with N-number of wells arranged in x-rows and y-columns.

Method 164 may be used to provide the following advantages for the pharmaceutical industry: (1) identify errors in pharmaceutical data due to physical errors in a screening system used to collect pharmaceutical data, or biological errors in an assay; (2) create rule based experts to improve pharmaceutical data (3) use automated reasoning to improve fused knowledge; and (4) improve the overall drug discovery process. Method 164 may also be used for purposes other than determining physical or biological errors (e.g., providing additional pattern matching expertise for previously undiscovered or unnoticed patterns, providing automated reasoning to improve fused knowledge, etc.).

It should be understood that the programs, processes, methods and systems described herein are not related or limited to any particular type of computer or network system (hardware or software), unless indicated otherwise. Various types of general purpose or specialized computer systems may be used with or perform operations in accordance with the teachings described herein.

In view of the wide variety of embodiments to which the principles of the present invention can be applied, it should be understood that the illustrated embodiments are exemplary only, and should not be taken as limiting the scope of the present invention. For example, the steps of the flow diagrams may be taken in sequences other than those described, and more or fewer elements may be used in the block diagrams. While various elements of the preferred embodiments have been described as being implemented in software, in other embodiments hardware or firmware implementations may alternatively be used, and vice-versa.

The claims should not be read as limited to the described order or elements unless stated to that effect. Therefore, all embodiments that come within the scope and spirit of the following claims and equivalents thereto are claimed as the invention.

We claim:

1. A method for interpreting experimental data with automated reasoning, comprising:
   acquiring domain specific knowledge from a plurality of pharmaceutical information sources;
   creating a semantic representation of the domain specific knowledge that meets a desired set of criteria;
   classifying pharmaceutical data from a knowledge database with the semantic representation;
   providing a set of reasons for any classified pharmaceutical data, wherein the set of reasons are used to help interpret the classified pharmaceutical data;
   creating a further semantic representation of the domain specific knowledge;
   classifying pharmaceutical data from the knowledge database with the further semantic representation; and
   creating fused knowledge from the classified pharmaceutical data.

2. A computer readable medium having stored therein instructions for causing a processor to execute the method of claim 1.

3. The method of claim 1 wherein the fused knowledge includes knowledge obtained from a plurality of domains from pharmaceutical industries fused into a multi-parameter output in a single parallel pass through the knowledge database.

4. The method of claim 1 wherein the step of creating a semantic representation of the domain specific knowledge that meets a desired set of criteria includes creating a semantic representation of a general screening expert, an instrument expert or an assay expert using a plurality of expert specific rules.

5. The method of claim 1 wherein the step of classifying pharmaceutical data from a knowledge database with semantic representation includes classifying pharmaceutical data based on determined physical errors from a screening process used to collect the pharmaceutical data.

6. The method of claim 5 wherein the physical errors include gel-electrophoresis errors, bio-chip errors, pipettor errors, microplate preparation errors or microplate variance errors.

7. The method of claim 1 wherein the step of classifying pharmaceutical data from a database with semantic representation includes classifying pharmaceutical data based on determined biological errors from an assay used to collect the pharmaceutical data.

8. The method of claim 1 wherein the step of providing a set of reasons for any classified pharmaceutical data includs providing a set of reasons as to why a detected pattern in the classified pharmaceutical data is an error pattern.

9. A method for interpreting experimental data with automated reasoning, comprising:

acquiring domain specific knowledge from a plurality of pharmaceutical information sources;

creating a semantic representation of the domain specific knowledge that meets a desired set of criteria;

classifying pharmaceutical data from a knowledge database with the semantic representation;

providing a set of reasons for any classified pharmaceutical data, wherein the set of reasons are used to help interpret the classified pharmaceutical data;

determining with the set of reasons whether any classified pharmaceutical data includes data related to physical errors or biological errors, and if so, marking classified pharmaceutical data related to physical errors or biological errors as unreliable in the knowledge database, thereby validating any fused knowledge created from the knowledge database.

10. The method of claim 5 wherein the step of creating a semantic representation of the domain specific knowledge that meets a desired set of criteria includes creating a semantic representation of a general screening expert, an instrument expert or an assay expert using a plurality of expert specific rules.

11. The method of claim 5 wherein the step of classifying pharmaceutical data from a knowledge database with semantic representation includes classifying pharmaceutical data based on determined physical errors from a screening process used to collect the pharmaceutical data.

12. The method of claim 11 wherein the physical errors include gel-electrophoresis errors, bio-chip errors, pipettor errors, microplate preparation errors or microplate variance errors.

13. The method of claim 5 wherein the step of classifying pharmaceutical data from a database with semantic representation includes classifying pharmaceutical data based on determined biological errors from an assay used to collect the pharmaceutical data.

14. The method of claim 5 wherein the step of providing a set of reasons for any classified pharmaceutical data includes providing a set of reasons as to why a detected pattern in the classified pharmaceutical data is an error pattern.

15. A method for interpreting experimental data with automated reasoning, comprising:

acquiring domain specific knowledge from a plurality of pharmaceutical information sources;

creating a semantic representation of the domain specific knowledge that meets a desired set of criteria, wherein the semantic representation includes plurality of rules to identify physical errors or biological errors in a plurality of screening processes used to collect pharmaceutical data;

classifying a plurality of errors patterns in pharmaceutical data from a knowledge database with the semantic representation;

providing a set of reasons for any classified pharmaceutical data, wherein the set of reasons are used to annotate error patterns to help interpret physical errors in the classified pharmaceutical data; and marking the classified pharmaceutical data as unreliable in the knowledge database, thereby validating any fused knowledge created from the knowledge database, wherein the fused knowledge includes knowledge obtained from a plurality of domains from pharmaceutical industries fused into a multi-parameter output in a single parallel pass through the knowledge database.

16. A computer readable medium having stored therein instructions for causing a processor to execute the method of claim 15.

17. The method of claim 15 wherein the physical errors include gel-electrophoresis errors, bio-chip errors, pipetter errors, microplate preparation errors or microplate variance errors and biological errors including assay errors.

18. The method of claim 15 wherein the step of creating a semantic representation of the domain specific knowledge that meets a desired set of criteria includes creating a semantic representation of a general screening expert, an instrument expert or an assay expert using a plurality of expert specific rules.

19. An automated reasoning creation and analysis system, comprising in combination:

an automated reasoning engine for acquiring domain specific knowledge from a plurality of pharmaceutical information sources, creating a semantic representation of the domain specific knowledge that meets a desired set of criteria, classifying pharmaceutical data from a knowledge database with the semantic representation, and providing a set of reasons for any classified pharmaceutical data, wherein the set of reasons are used to help interpret the classified pharmaceutical data, creating a further semantic representation of the domain specific knowledge, classifying pharmaceutical data from the knowledge database with the further semantic representation, determining with the set of reasons whether any classified pharmaceutical data includes data related to physical errors or biological errors, and if so, marking classified pharmaceutical data related to physical errors or biological errors as unreliable in the knowledge database, thereby validating any fused knowledge created from the knowledge database, and wherein the fused knowledge includes knowledge obtained from a plurality of domains from pharmaceu tical industries fused into a multi-parameter output in a single parallel pass through the knowledge database;

plurality of domain specific knowledge from a plurality of pharmaceutical information sources; and a knowledge database for storing raw experimental data and knowledge derived from raw pharmaceutical data.

20. The system of claim 19 wherein creating semantic representation includes creating a semantic representation of a general screening expert, an instrument expert or an assay expert using a plurality of expert specific rules.

* * * * *